(12) United States Patent
Osborn, III et al.

(10) Patent No.: US 7,937,249 B2
(45) Date of Patent: May 3, 2011

(54) COMPUTATIONAL MODEL OF THE INTERNAL HUMAN PELVIC ENVIRONMENT

(75) Inventors: Thomas Ward Osborn, III, Clifton, OH (US); Ryo Minoguchi, Blue Ash, OH (US); Hyundae Hong, West Chester, OH (US); Steven J Owens, Loveland, OH (US); Balakrishna Haridas, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1557 days.

(21) Appl. No.: 11/181,280

(22) Filed: Jul. 14, 2005

(65) Prior Publication Data
US 2007/0027667 A1 Feb. 1, 2007

(51) Int. Cl.
G06F 17/50 (2006.01)
G06F 19/00 (2006.01)

(52) U.S. Cl. ............... 703/2; 702/42; 600/300; 700/98
(58) Field of Classification Search ...... 703/2; 600/407, 600/443, 424, 300; 702/42; 700/98
See application file for complete search history.

(56) References Cited

U.S. PATENT DOCUMENTS

| 4,349,033 A | 9/1982 | Eden |
| 4,566,465 A | 1/1986 | Arhan |
| 5,167,237 A | 12/1992 | Rabin |
| 5,433,216 A | 7/1995 | Sugrue |
| 5,592,085 A * | 1/1997 | Ehman ........................ 324/309 |
| 5,674,238 A | 10/1997 | Sample |
| 5,984,879 A | 11/1999 | Wallace |
| 6,063,045 A | 5/2000 | Wax |
| 7,203,604 B2 * | 4/2007 | Mazilu ........................... 702/42 |
| 7,308,387 B1 * | 12/2007 | Feng et al. ..................... 703/1 |
| 2002/0168618 A1 * | 11/2002 | Anderson et al. ............ 434/262 |
| 2004/0210136 A1 * | 10/2004 | Varghese et al. ............. 600/443 |
| 2005/0143967 A1 | 6/2005 | Holberg |
| 2005/0165284 A1 * | 7/2005 | Gefen ........................... 600/300 |
| 2005/0165471 A1 * | 7/2005 | Wang et al. .................. 623/1.15 |
| 2005/0188770 A1 * | 9/2005 | Mazilu ........................... 73/826 |
| 2005/0264561 A1 | 12/2005 | Anast et al. |
| 2005/0264562 A1 | 12/2005 | Macura et al. |
| 2005/0264563 A1 | 12/2005 | Macura et al. |
| 2005/0264572 A1 | 12/2005 | Anast et al. |
| 2005/0267613 A1 | 12/2005 | Anast et al. |
| 2005/0267614 A1 | 12/2005 | Looney et al. |
| 2005/0267615 A1 | 12/2005 | Lavash et al. |
| 2006/0278245 A1 * | 12/2006 | Gan ............................. 128/898 |
| 2007/0167704 A1 * | 7/2007 | Chance ........................ 600/407 |

OTHER PUBLICATIONS

"A 3D biomechanicl model for numerical simulation of dynamic mechanical interactions of Bra and Breast during wear", Li Y et al., Sen I gakkaishi, Tokyo, JP, vol. 59, No. 1, 2003, pp. 12-21.

(Continued)

*Primary Examiner* — Thai Phan
(74) *Attorney, Agent, or Firm* — Megan C. Hymore; James E. Oehlenschlager; Roddy M. Bullock

(57) ABSTRACT

A computational model of the internal human pelvic environment. The model comprises meshed finite element regions corresponding to internal tissues or organs selected from the group consisting of pelvic muscles, vagina, vaginal walls, intestinal tissues, bowel tissues, bladder, bladder walls, cervix, and combinations thereof.

14 Claims, 16 Drawing Sheets

OTHER PUBLICATIONS

"A three-dimensional model of the mandible using two-dimensional CT images", Mutlu-Sagesen L. et al., Proceedings of the 23rd Annual International Conference of the IEEE Engineering in Medicine and Biology Society, Istanbul, Turkey, Oct. 25-28, vol. 1 of 4, Conf. 23, Oct. 25, 2001, pp. 2778-2781.

E.M.H. Bosboom, Passive transverse mechanical properties of skeletal muscle under in vivo compression, Journal of Biomechanics 34 (2001) 1365-1368.

Can A. Yucesoy, Three-dimensional finite element modeling of skeletal muscle using a two-domain approach; linked fiber-matrix mesh model, Journal of Biomechanics 35 (2002) 1253-1262.

* cited by examiner

US 7,937,249 B2

COMPUTATIONAL MODEL OF THE INTERNAL HUMAN PELVIC ENVIRONMENT

FIELD OF THE INVENTION

This invention relates to the measurement and determination of biomechanical properties of internal tissues or organs of a living body, such as a human body.

BACKGROUND

Understanding the biomechanical properties of body tissues, particularly internal tissues or organs, is useful for the development of improved medical diagnostic and treatment tools. In addition, understanding the biomechanical properties such as the elastic and visco-elastic properties of internal tissues or organs can aid in designing more safe, comfortable and effective devices for internal use. Biomechanical implications learned from these measurements can improve not only the design of medical devices and implants used for minimally invasive surgery, but also any other products interacting with body tissues. As an example, knowledge of biomechanical properties can help in developing a better understanding of the effects of internally worn devices such as tampons on the deformations in internal tissues to the point of affecting comfort and effectiveness.

External tissues and organs such as the stratum corneum and epidermis can be relatively easily characterized for in vivo mechanical properties because of easy accessibility and locating the point of measurement. However, internal tissues and organs, such as intra-abdominal tissues, intra-vaginal tissues, intra-uterine tissues, intra-esophageal tissues, and the likes are more difficult to characterize. In particular, in-vivo measurements of internal tissues to obtain biomechanical properties are difficult due to limited accessibility nature of such tissues and difficulties associated with locating the point of measurement. The constraints of available devices and techniques to reach these tissues, as well as the difficulty of obtaining accurate data under in vivo condition has hampered efforts at accurately modeling of 'living' internal tissue biomechanical properties.

In-vivo measurements of internal tissues properties of organs such as the vagina are particularly difficult to achieve. The human female vagina is located in the lower pelvic cavity and surrounded by the major organs such as the uterus, the bladder, and the rectum. The vagina is a collapsed tube-like structure composed of fibromuscular tissue layers. The central portion has an H-shaped cross section and its walls are suspended and attached to the paravaginal connective tissues. The vaginal inner walls have rugal folding which is extended significantly during delivery. Smooth muscle fibers are oriented along the vaginal axis and arranged circularly toward the periphery. Vaginal walls are connected to the lateral pelvic floor by connective tissues and smooth muscle layers, which allow the vagina deformed and displaced easily according to the external strain energy applied.

The pelvic environment comprises a soft tissue and muscle "hammock" to which the various organs are attached. For example, the vagina is connected to the pelvis by the pelvic floor muscles and connective tissue. Because of it location within pelvic cavity, the degree of vaginal tissue deformation is significantly influenced by the biomechanical properties of surrounding organs and tissues. Furthermore, because there is no rigid supporting structure around the vagina, but connective tissues of smooth muscle fibers among the surrounding organs, it is important to understand not only deformation of vaginal tissues, but also surrounding organs' boundaries for complete measurement of biomechanical properties and parameters of vaginal and surrounding tissues. Among the surrounding organs of vagina, the bladder is the most influential organ in a way that the vaginal tissue responds to external strain; as the bladder expands by accumulating urine, it stretches toward vesicovaginal tissue layers. The apparent physical change is deformation (stretching and/or compaction) of tissue layers, which can in turn impact the stiffness of tissue layers. Interactions among the lower pelvic floor organs make the in vivo measurement of vaginal tissue more challenging work. Therefore, these anatomical complexities of the vagina and surrounding tissues and organs require that biomechanical properties be obtained by considering the heterogeneous and inhomogeneous nature of the related human anatomy, and interactions of neighboring organs and tissues.

Accordingly, there is a continuing unaddressed need for better devices and methods for determining biomechanical properties of internal tissues and organs. The new measurement method is preferably non-invasive or at least minimally invasive, so the mechanical properties of the original tissues are well maintained while the measurement is underway.

Further, there is a continuing unaddressed clinical need for devices and methods for measuring biomechanical tissue properties in-vivo, such that the effects of surrounding tissues and organs are taken into account.

Additionally, there is a continuing unaddressed need for a device and method for determining the biomechanical properties of different portions of the same tissue or organ.

SUMMARY OF THE INVENTION

A computational model of the internal human pelvic environment is disclosed. The model comprises meshed finite element regions corresponding to internal tissues or organs selected from the group consisting of pelvic muscles, vagina, vaginal walls, intestinal tissues, bowel tissues, bladder, bladder walls, cervix, and combinations thereof.

DETAILED DESCRIPTION OF THE INVENTION

The method and device of the present invention overcomes the technical challenges and problems associated with determining in vivo the biomechanical properties of tissues. In particular, the method and device of the present invention can be used to determine location dependent biomechanical properties, i.e., properties that are specific to a particular location in the body and/or on a particular tissue. The method and device of the present invention can include a measurement system in a combined format of a strain gauge type physiological pressure transducer to measure the tissue loading stress, and imaging devices such as a CT, a magnetic resonance imaging (MRI), or an ultrasound imager to measure localized tissue strain profiles. Such imaging devices permit non-invasive, externally disposed probes to be utilized for the purpose of making measurements of static or dynamic tissue deformation. The method of the present invention also comprises a modeling internal tissues of a body by numerical methods, including finite element analysis.

Figure 1A:
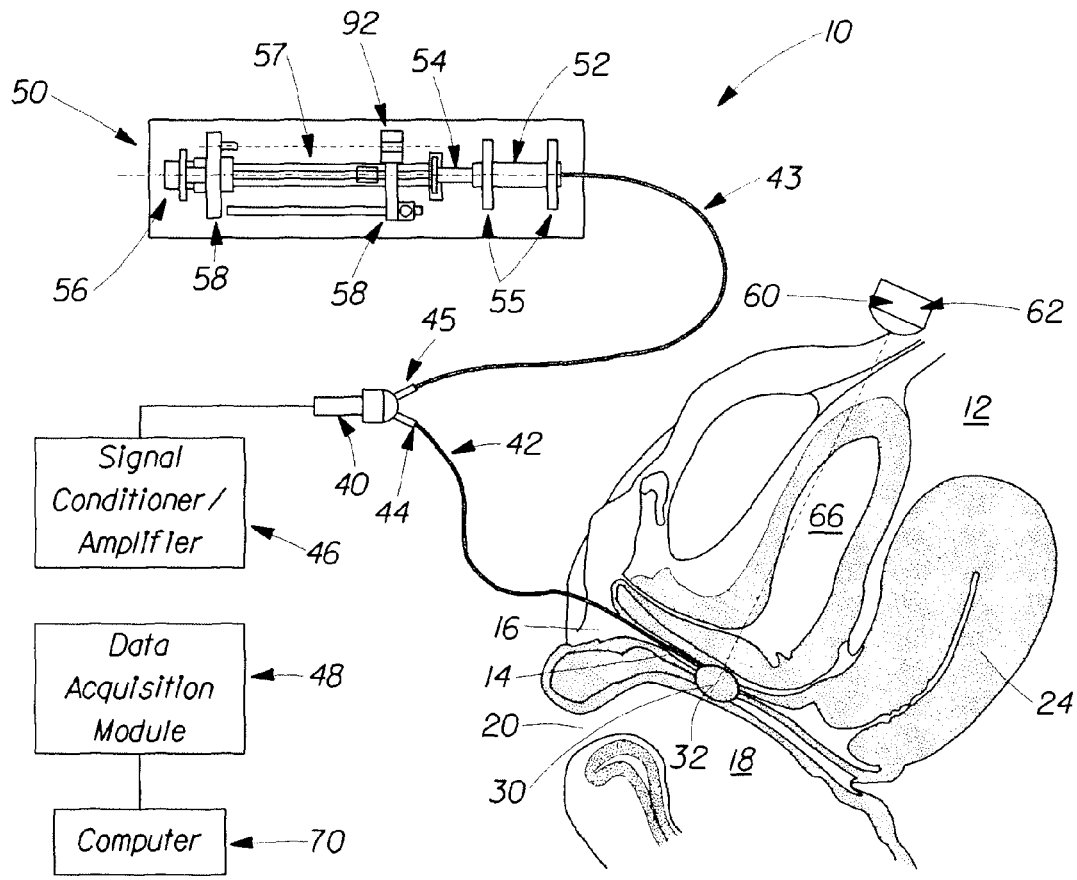
FIG. 1 is a schematic representation of a device of the present invention and some key measurement positions along the vagina axial path.

A device of the present invention is shown in FIG. 1(a), which shows a device 10 of the present invention that can be used to determine biomechanical properties of internal tissues of a body 12 which can be a human or an animal. The device 10 can be used to measure biomechanical properties inside the vagina 14 of a female. However, the device 10 can be used to determine biomechanical properties of any internal tissues and organs that can be accessed through body orifices sufficiently large for insertion of the internally-disposed portions of the device.

Figure 1B:
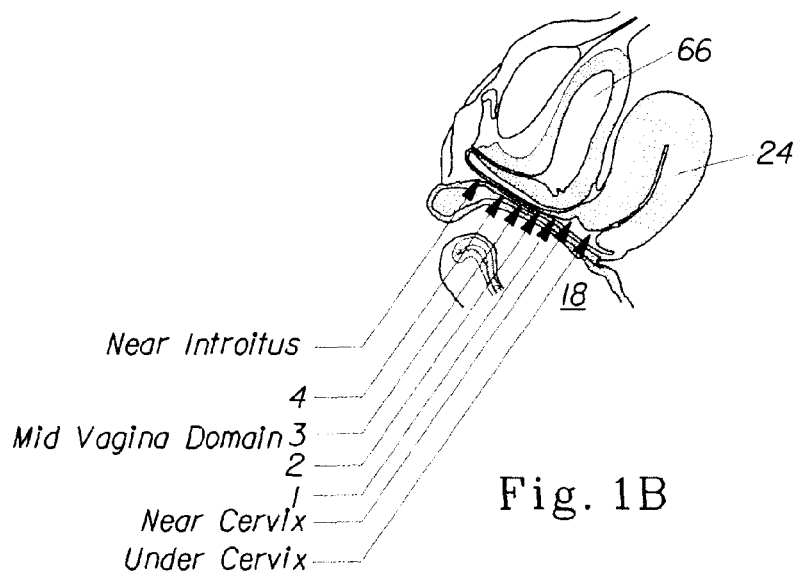

The device 10 of the present invention can be used to measure stress and strain of internal tissues. For example, when used to measure vaginal tissue properties, as in the embodiment illustrated herein, representative stress and/or strain measurement positions can be those shown in FIG. 1(b) from "Near Introitus" to "Under Cervix" along the axial direction of vaginal path toward cervix. However, measurement of stress and strain profiles can be done anywhere along the vaginal path as long as the imaging modality can visualize the location properly for the strain analysis. The location can be easily identified when the imaging modality shows the vagina and surrounding organs clearly. Two fiducial points, ie., the introitus and the cervix can be identified first and then the entire vaginal path can be divided into six sections as shown in FIG. 1(b), such as sections 1, 2, 3, and 4 associated with the mid-vagina, and a section labeled as near cervix.

The device 10 includes at least four main parts: an expandable tissue strain device 30, a pressure transducer 40, a fluid volume controller 50, and an imaging device, which can be an external imaging device 60, 62. The expandable tissue strain device 30 can be a probe, such as an inflatable probe comprising medical grade elastomers such as urethane or latex that induces strain to tissues. Both urethane and latex can have very low moduli, about 2-2.5 M Pa, with latex exhibiting a modulus of about 2.2 MPa under a 500% extension from its original dimension. Suitable urethane elastomers can be purchased from Advanced Polymers Inc. as 25000001AB low durometer urethane.

In the illustrated embodiment the expandable tissue strain device 30 is an inflatable latex balloon 32. Latex balloon 32 can be sized so as to fit into the necessary body opening. In the illustrated embodiment, latex balloon 32 can fit through and into the female vagina 14 as shown in FIG. 1(a). Latex balloon 32 can be made from surgical latex material, and can comprise the finger portion of a latex glove. For example, in one embodiment, latex balloon comprises the fifth finger (i.e., the pinky finger) of a Microtouch® latex surgical glove, size 6, lot number 124-937, purchased from Johnson & Johnson. The size of latex balloon 32 can be varied as appropriate for the intended body opening. In the illustrated embodiment, latex balloon 32 can have an internal volume of between about 0 ml (when totally collapsed) to about 30 ml. Testing has shown that for that range of volume change, the average axial dimension (i.e., the diameter for a round balloon) can change from about 10 mm to about 40 mm.

Strain transducer 30, such as inflatable latex balloon 32, can be operatively connected to a pressure transducer 40 by any suitable means, including by tubing 42. Tubing 42 can be relatively rigid tubing, such that pressure differentials have little or no effect on tubing volume. In one embodiment tubing 42 has a modulus at least twice that of strain transducer 30, such as inflatable latex balloon 32. In this manner, pressure changes applied on the inserted balloon 32 can be accurately detected by pressure transducer 40. In one embodiment latex balloon 32 is attached to VWR Brand® 5/32 inch ID PCV tubing, catalog number 60985-516, FDA/USDA/USP-VI Certified Lab/Food/Medical Grade available from VWR International Inc. (West Chester, Pa.).

Figure 2A:
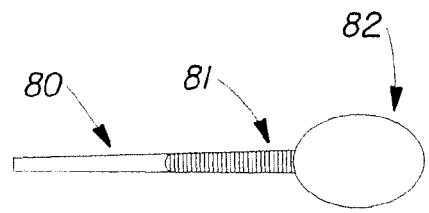
FIG. 2 is a one embodiment of tissue strain device, in this case, a latex balloon attached to a closed line of fluid.

As shown at FIG. 2(a), the latex balloon 32 can be joined to tubing 42 in any suitable manner sufficient to hold a pressure tight seal over the range of pressures required for the particular body portion of interest. In one embodiment the latex balloon was joined to the tubing by placing the open end of the balloon over the end of a section of PVC tubing, wrapping with orthodontic rubber bands available from Ormco Z-pak Elastics (Ormco Corp. Glendora, Calif.), and then overwrapping with Tagaderm® tape, 81, as shown in FIG. 2(a). Tagadermg tape, available from 3M (St. Paul, Minn.) was added in an amount sufficient to ensure a pressure tight seal, that is, sufficient to seal against pressure losses over the range of pressures required for the particular body portion of interest.

Figure 2B:
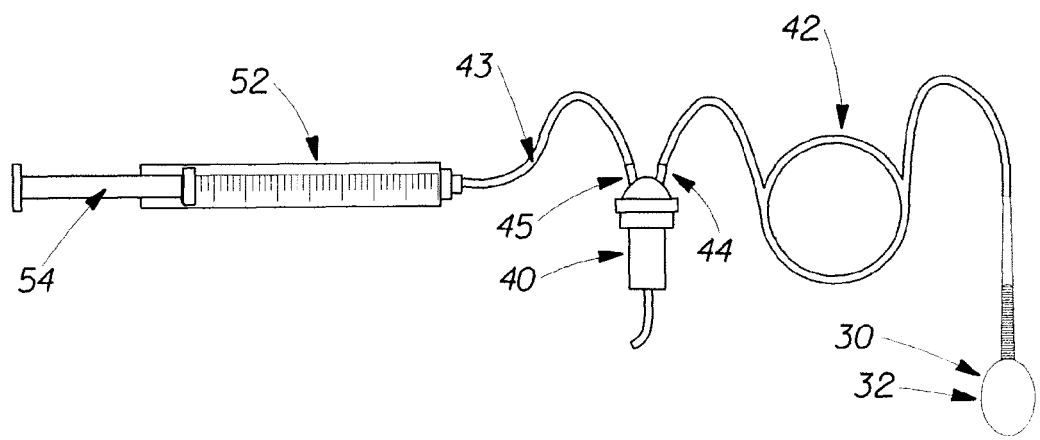

The other end of the tubing 42 is operatively connected to an input port 44 of pressure transducer 40, as shown in FIG. 1(a) and FIG. 2(b). Connection can be by any suitable means, including adhesive attachment, tape sealing, or thermal melt bonding. Pressure transducer 40 can be any of known static/dynamic strain gauge type pressure transducers for detecting changes in fluid pressure inside tubing. For the sake of safety to a body, 12, a medical grade pressure transducer can be utilized. In one embodiment, pressure transducer 40 is a Gould Spectramed® Model P23ID physiological pressure transducer available from Gould (Valley View, Ohio). Pressure transducer 40 generates signals that can be amplified and filtered through a signal conditioning amplifier 46. Signal conditioning amplifier 46 can be any of known signal amplifiers suitable for strain gauge type pressure transducers, and in one embodiment it can be a physiological pressure transducer amplifier, DA 100C available from BIOPAC® Systems, Inc (Goleta, Calif.). The BIOPAC® signal conditioning amplifier can be used with companion modules such as isolated power supply module, IPS100C and output signal isolator, OUTISO available from the same manufacture. Amplified and filtered signals can then be digitized by use of a data acquisition module 48, such as a USB Function Module for data acquisition, DT9803, available from Data Translation Inc. (Marlboro, Mass.). Once signals are digitized, they can be collected, analyzed, or otherwise manipulated by means of a computer 70.

A second port, such as output port, 45 of pressure transducer 40 is joined to tubing 43 that can be identical to tubing 42. Tubing 43 connects pressure transducer 40 to fluid volume controller 50. Fluid volume controller 50 can be any of known devices for managing the volume of fluid present in the device 10, particularly the volume and rate of change of volume of an expandable tissue strain device 30 such as an inflatable balloon 32. Tubing 43 can be joined in any suitable manner at both ends, including by adhesive attachment, tape sealing, or thermal melt bonding.

In one embodiment shown in FIG. 1A, the fluid volume controller 50 comprises a syringe device comprising a syringe housing 52, a syringe plunger 54 and mounting hardware including any of various known clamps 55. Syringe housing 52 can have any suitable volume for the intended purpose; various sizes of syringes are available to meet the various volume change needs. In one embodiment syringe housing 52 has a volume of 50 ml. Syringe plunger 54 can be operated manually. However, for greater accuracy of measured parameters, syringe plunger 54 can be linearly positioned by syringe plunger pushing device 56 that can comprise any of known linear positioning devices, such as drive shaft 57 mounted on linear shaft guide as known in the art.

Figure 3A:
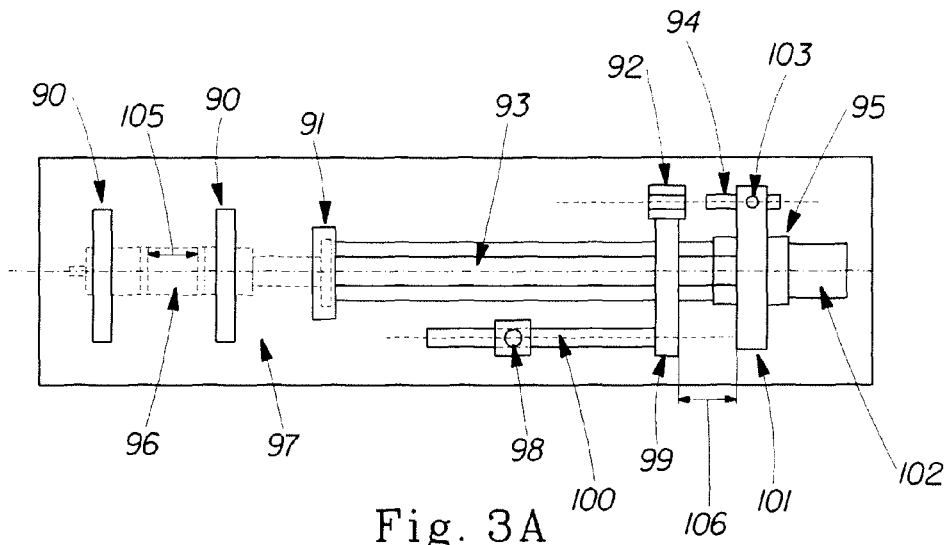
FIG. 3 is a schematic representation of manual operation and stepping-motor driven fluid volume controllers.

The fluid volume controller 50 shown in FIG. 1(*a*) operates in a similar manner as a simple syringe-type mechanism as shown in FIG. 2(*b*). However, for precision control of fluid volume increase in the balloon 32, two different embodiments of fluid volume controller can be used: manual positioning of syringe plunger 54 as shown at FIG. 3(*a*) and automatic means as shown with reference to FIGS. 3(*b*) and 3(*c*). Fluid volume controller 50 can be operated by manual control of syringe volume, 96. Before the operator pushes the manual pushing plate 101, he or she can adjust the pushing plate positioning guide 102 to set the initial syringe volume position, which allows repeatable volume change. The net change of syringe volume is determined from the stroke length 105 of the syringe plunger 54. The plunger stroke is matched with travel distance 106 of manual pushing plate 101. This travel distance is in turn set by the adjustable limiter positioning guide 100. Once the operator determines the desired volume change, distance 106 can be set by securing limiter clamp 98, thereby making volume change repeatable. Because both the syringe drive shaft 93 and syringe plunger 105 are conjoined by the syringe coupling 91, the movement of manual pushing plate 101 and syringe plunger 105 are synchronized. These controlled mechanical motions drive the syringe 52 of FIG. 2(*b*) or 96 FIG. 3(*a*) in a controlled and repeatable manner, and maintain the strain energy applied on the tissue at a predetermined and calibrated level.

The syringe plunger pushing device 56 of FIG. 1(*a*) can be either a manual pushing mechanism as described above and shown in FIG. 1(*a*) and FIG. 3(*a*), or a motor driven system as shown in FIGS. 3(*b*) and 3(*c*). Motor driven systems can use a stepper motor to control the volume change rate more precisely. In one embodiment the stepping motors can be a DRL Series Compact Linear Actuator and Driver System from the Oriental Motors (Torrance, Calif.).

Figure 3B:
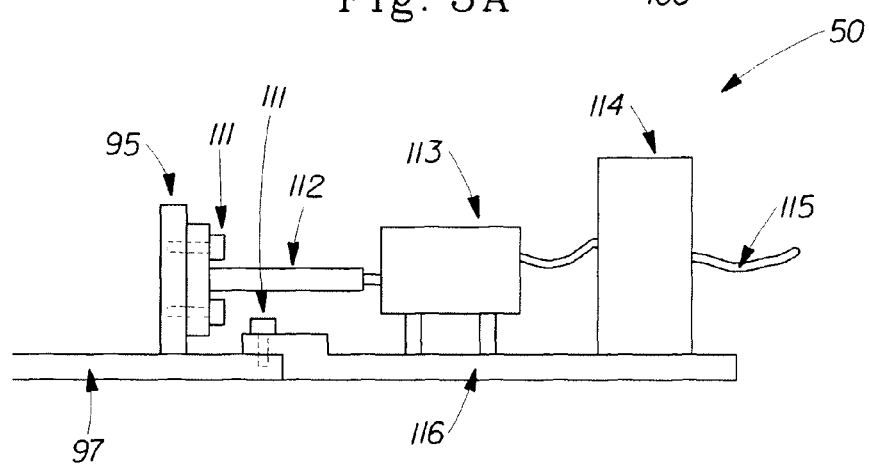
Figure 3C:
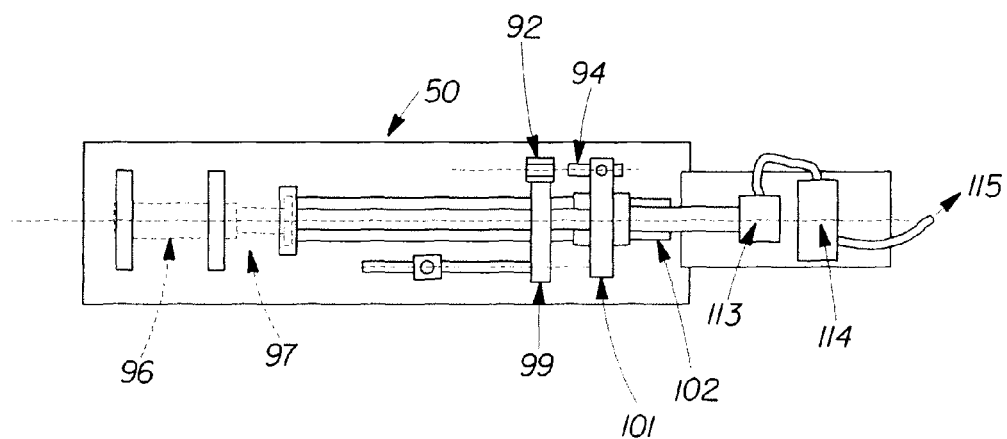

FIG. 3B shows a linear actuator stage 116 that includes an actuator motor 113 and a motor controller 114 coupled to plunger pushing handle 95 with simple mating screws 111. As shown at FIG. 3(*b*) and 3(*c*), the linear motion generated by the linear actuator motor, 113, is delivered to the existing plunger pushing handle, 95 through a connecting rod, 112. Therefore, this design allows easy attachment and detachment of motor driven fluid volume controller according to the necessary test protocols. In one embodiment a computer control signal 115 generates the control signal to operate the linear motion motor 113. Computer control signal 115 can be from a program specifying a specific tissue strain protocol. Linear motion is transferred to syringe drive shaft 93 of FIG. 3(*a*) which drives syringe plunger 54 of FIG. 2(*b*). Precision control of fluid volume is particular useful for the measurement of creep and relaxation of viscous property of tissue.

As shown in FIG. 3(*a*), an optical switch 92 detects the moment when the syringe plunger 54 of FIG. 2(*b*) travels a predetermined distance, i.e., a stroke length. Optical switch 92 can generate a digital compatible signal that can be sent to the data acquisition module 48 of FIG. 1(*a*). The optical switch 92 is structurally one body with a limiter arm 99 and a limiter positioning guide 100. Therefore, when the stroke length 106 is adjusted by moving the limiter positioning guide 100, the optical switch 92 is positioned in new location. Once the stroke length is adjusted, the new position is locked up by limiter clamp 98. The plunger activation signal is generated when the light path of the optical switch 92 is blocked by the optical switch activator 94, which can be a protrusion that can move into the path of a light beam, thereby actuating optical switch 92. The optical switch activator can be set so it blocks the light path at the moment when the manual pushing plate 101 is touched to the limiter arm 99. Once the appropriate standoff distance of the optical switch activator 94 is found, the position is locked up by the optical switch activator clamp 103.

Figure 4:
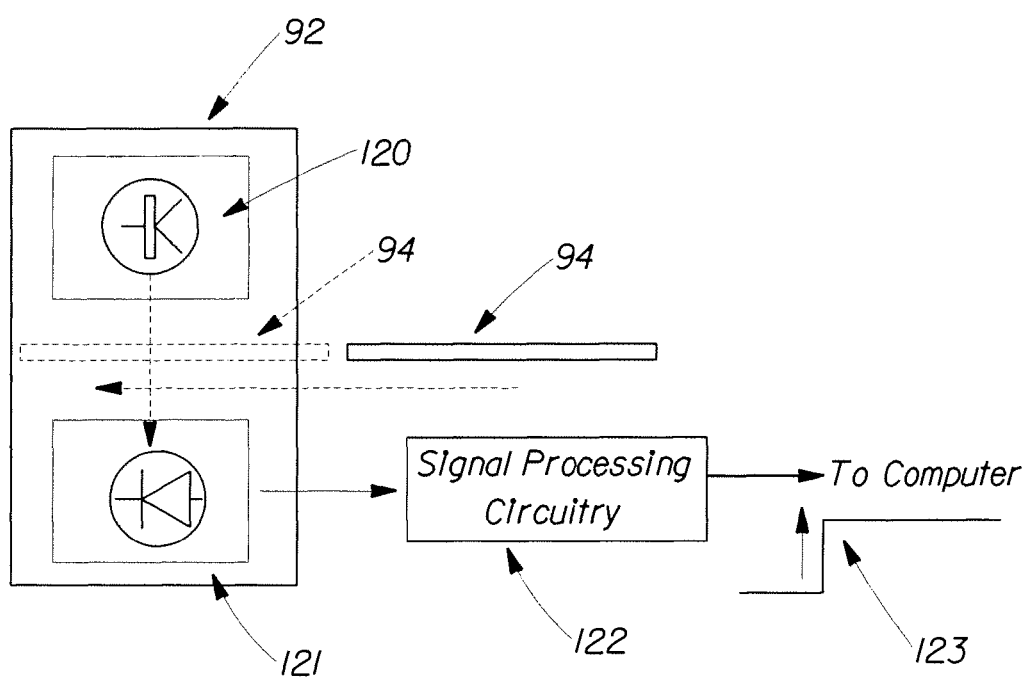
FIG. 4 is an optical switch and its signal generated for the temporal alignment of stress signals.
Figure 11A:
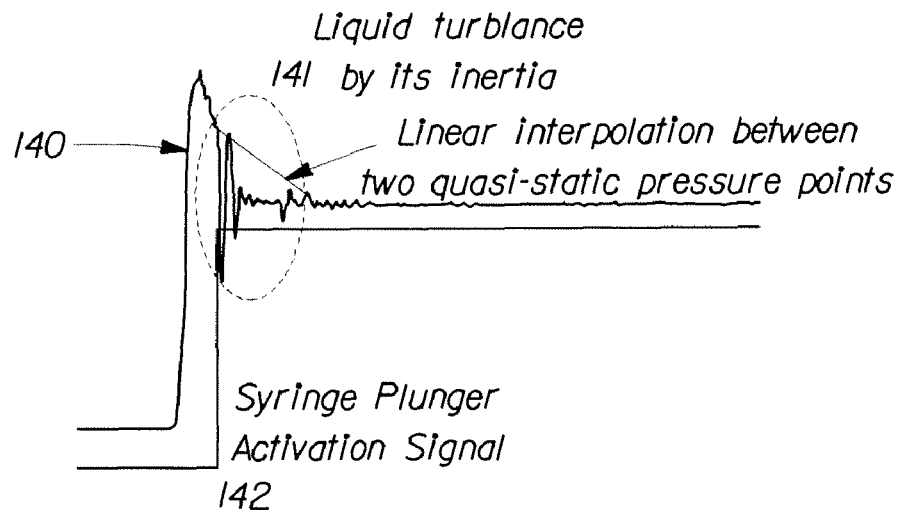
FIG. 11 is the concept of transient stress signal analysis for the measurement of viscosity related parameters of in vivo tissue.
Figure 11B:
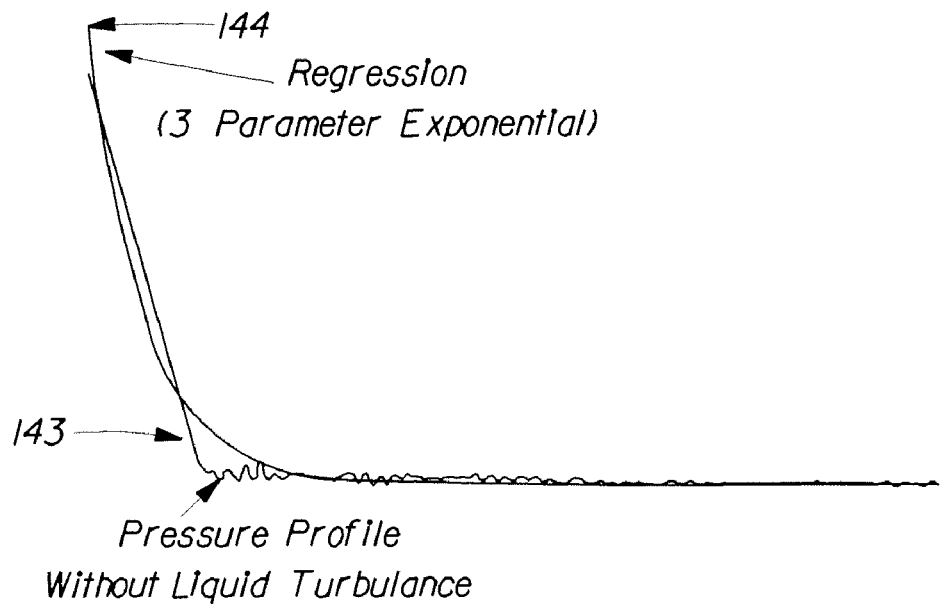

Signals from the optical switch 92 permit signal processing programs to accurately align the signal profiles in the time domain and measure the stress relaxation time. Such measurements are particularly beneficial to measure the viscous property of internal tissues, such as vaginal tissue layers. Any optical switch sensor known in the art and capable of providing digital output can be utilized. In one embodiment, a model OPB-855 phototransistor type optical switch from Optek Technologies Inc (Carrollton, Tex.) was used. The principle of the optical switch operation for this specific embodiment is shown at FIG. 4. When the plunger drive shaft 93 pushes the syringe plunger, the optical switch activator 94 travels through the opening slot of the optical switch 92. Once the optical switch activator 94 moves into the slot it blocks the light passage from the phototransistor 120 to the photodiode 121. This light blockage causes the signal output of the photodiode 121 to change. This change in signal level is detected by the signal processing circuitry, 122, and generates the digital signal 123. Digital signal 123 is treated as a syringe plunger activation signal 142 which is shown at FIG. 11(*a*), with other stress signals.

The fluid used to actuate a strain transducer can be gas or liquid. In one embodiment liquid is used to inflate an inflatable balloon 32. In one embodiment the liquid can be water or saline solution. As a technical matter, the choice of gas or liquid is important with respect to the imaging modality (as discussed below). In the case of ultrasound imaging, a liquid is preferred because of ultrasound attenuation by a gas phase medium. With CT imaging or MRI imaging, there is less signal attenuation in a gaseous medium.

The operation of the device as discussed so far can be explained as follows. In one embodiment balloon 32 is made with a highly elastic latex material. The balloon has non-zero modulus, therefore, when the balloon is forced to expand by fluid volume controller 50, thereby increasing balloon strain, the balloon experiences stress increase and as a result, the internal pressure of the entire tubing line shown at FIG. 2(b) increases. This pressure increase is detected by the pressure transducer 40. This measurement is the in vitro balloon pressure.

Once the balloon is situated in an internal body cavity, such as the vagina 14, tissue loading can cause the balloon to experience a net volume reduction, ΔV, which in turn increases the internal pressure of the entire tubing line shown in FIG. 2(b). All the components of the apparatus except the inserted balloon are relatively inelastic; therefore, once the balloon experiences very small compressive force by tissue loading, the balloon deforms. As a result, the volume reduction, even a slight volume reduction (and isothermal) results in a pressure increase within the tubing line. This pressure change is detected by the pressure transducer 40.

In a similar manner, when the syringe plunger 54 pushes a certain volume of liquid from syringe housing 52, the balloon 32 absorbs this syringe volume reduction and increases its size. As the balloon 32 increases its size, it applies strain energy on the vaginal tissue layers. If the internal body tissue is highly elastic, which is the case for vaginal tissue, most of the strain energy is absorbed by the tissue and the balloon can expand to the size of the in-vitrQ (i.e., no tissue existing) condition. However, if the tissue is highly inelastic, the tissue is not deformed much and most of the strain energy is absorbed by the balloon, and as a result, it increases the internal pressure significantly because volume reduction by the syringe plunger is not compensated unless the balloon absorbs that strain energy. Therefore, for the same syringe volume reduction, relatively inelastic tissue causes reduced rate of volume (or diameter) increase of the inserted balloon; therefore, net volume change of the entire tubing line is large and as a result, a higher pressure is experienced.

Imaging device 60 can be any of known medical grade imager to image a living body, including CT scanner, MRI devices and ultrasound devices. In one embodiment, such as the one shown in FIG. 1(a), the imaging device 60 comprises an externally-disposed probe, such as an ultrasound probe 62 of a Voluson 730® ultrasound imager from Medison-GE Healthcare (Waukesha, Wis.). Imaging means 60 permits visual or digital imaging of tissues and organs, and detects changes in position that can be correlated to the strain of tissues and organs. Ultrasound imaging can operate in M (motion)-mode for imaging or B (brightness)-mode for regular anatomical imaging of lower pelvic floor.

Device 10 works in principle by correlating pressure changes and rates of change of pressure within the tissue strain device 30 (i.e., a balloon) to the strain and rates of strain changes of tissues and/or organs. Pressure can be measured directly via pressure transducer 40 while imaging device 60 can measure tissue strain by measuring changes in position or changes in dimensions of tissues or organs. The pressure signal is evaluated to estimate the loading stress applied on a defined in-vivo area, thereby later enabling the calculation of material parameters such as modulus of tissues and/or organs. Such a device is useful, for example, for determining tissue properties required for modeling the insertion, expansion, and pressure application of a device penetrating the vaginal orifice, such as a tampon inserted into a vagina.

Method of Use

In general, the method of use includes inserting the tissue strain device, 30, into a body cavity of interest, directing the imaging means to detect dimensional changes at the area of interest, changing the volume of the tissue strain device by forcing fluid from the fluid volume controller and into the tissue strain device, detecting and measuring changes in pressure, detecting and measuring changes in position or dimension of the tissue or organ of interest, and correlating the measured parameters to determine biomechanical properties of internal tissues and/or organs.

Prior to inserting an inflatable probe, i.e., inflatable balloon 32, into the body cavity of interest, the in-vitro modulus of inflatable probe can be measured. By determining the in-vitro modulus of inflatable probe and measuring the pressure required to inflate the probe in-vitro, the net modulus and net pressure caused by the in-vivo volume expansion of the inflatable probe can be more accurately calculated by subtracting the in-vitro modulus and pressure from the in-vivo modulus and pressure.

In one embodiment latex balloon 32 has a relaxed, un-inflated volume of about 0 to about 3 ml. Latex balloon 32 can be slightly inflated with water or saline solution to about 5 to 10 ml prior to insertion into the desired body cavity. For example, balloon 32 can be slightly pressurized to give some stability to the balloon and assist in insertion into the vagina through the vaginal opening. Once inserted into the desired body cavity, e.g., the vagina, imaging means can be utilized to image the portion of the body in which the inflatable probe is to be expanded to induce strain to nearby tissues and organs.

The location of the inflatable probe can be verified by utilizing an ultrasound imaging means, used with ultrasound B mode. In one embodiment, the ultrasound probe 62 can be a Voluson 730® Abdominal Transducer, Model RAB4-8, operated at about 560 micron resolution. In addition to verifying the location of inflatable probe, e.g., inflatable balloon 32, the ultrasound image can detect and record the corresponding position of tissue boundaries. Thus, for example, in addition to imaging the inflatable balloon 32 and a portion of the vagina, ultrasound imager images the bladder wall, a portion of the uterus, cervix, and some of the rectovaginal tissue layers.

Syringe plunger 54 of fluid volume controller 50 can be actuated so as to force fluid, such as water or saline solution, through tubing sections 42 and 43 and into inflatable balloon 32. As inflatable balloon 32 contacts and deforms adjacent vaginal tissue layers, any resulting increase in pressure is measured and recorded by pressure transducer 40 and any accompanying devices to translate the pressure into computer-readable data. Such accompanying devices can include signal conditioning amplifier 46, and data acquisition module 48.

As inflatable balloon 32 contacts and deforms adjacent tissue layers, imaging means can detect and record deflection, deformation, or other changes in tissues or organs. In one embodiment, ultrasound imaging device can be used in M-mode during the inflation or deflation process of an inflatable balloon 32. While permitting higher quality of tissue motion profile, the M-mode only works at certain scanning paths, i.e., one-dimensional paths for a one-dimensional scanning profile. In another embodiment, B-mode based strain analysis can be used. Most ultrasound imagers have video mode (Cine mode) of image recording, therefore, analysis of time dependent tissue deformation is possible.

Imaging means can capture information about tissue strain and/or tissue strain rate. Net tissue displacement can be determined as well as net displacement or deformation of tissue boundaries and adjacent organs. In particular, B-mode imaging can be used to determine net tissue deformation and M-mode imaging can be used to calculate dynamic tissue strain. Further, using Cine operation of B-mode in the Voluson 730® ultrasound imager, it is possible to acquire time dependent tissue deflection profiles with proper image analysis. This method can be useful for the measurement of creep phenomena of vaginal tissue layer, for example.

As shown in FIG. 5, tissue strain and deformation profiles can be obtained by use of both B- and M-mode ultrasound images. Voluson 730® ultrasound imager can provide both B- and M-mode images on the same screen to aid in understanding where to monitor the tissue motion profile. FIG. 5(a) shows a B-mode axial view and FIG. 5(c) shows a B-mode sagittal view of a vagina and surrounding tissues. FIGS. 5(b) and 5(d) are the M-mode images along the scanning paths shown at FIGS. 5(a) and 5(c), respectively. The M-mode is an ultrasound representation for time and tissue motion profile. The M-mode image of FIG. 5(b), for example, shows periodic tissue strain profiles along the scanning path shown at FIG. 5(a). The horizontal axis in the images of FIG. 5(b) and 5(d) represents the temporal scale, while the vertical axis represents the geometric scale along the scanning lines shown at FIGS. 5(a) and 5(c).

Bladder 66 is clearly visible at both B- and M-mode images of FIG. 5. The vesicovaginal and rectovaginal tissue layers are shown at 67 and 68, respectively. The image also shows the in-vivo tissue strain device 30, in this case, a balloon 32. The rate of tissue deformation, axial strain, can be measured from the images shown at FIGS. 5(b) and 5(d).

Figure 5A:
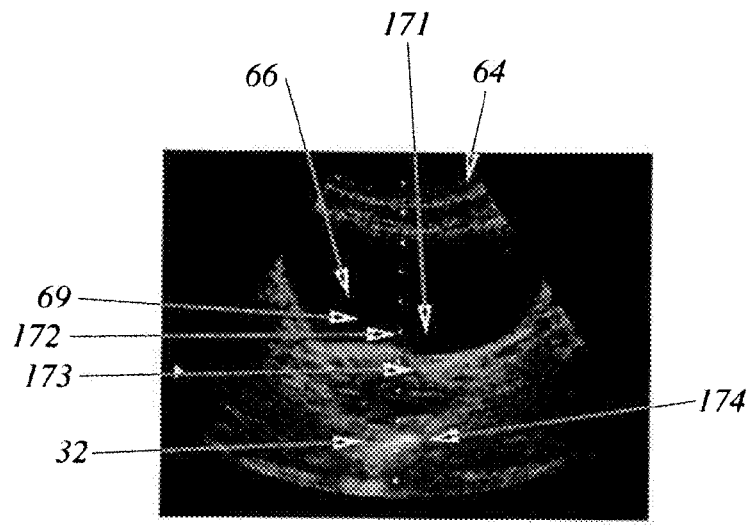
FIG. 5 is an illustrative representation of an ultrasound image that was found useful example for the present invention.
Figure 5B:
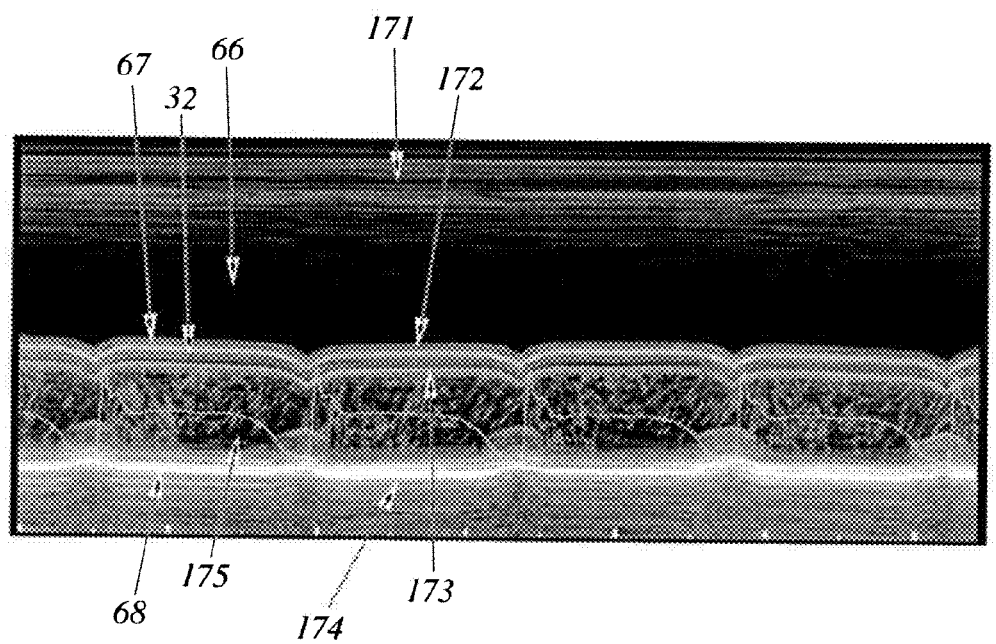
Figure 5C:
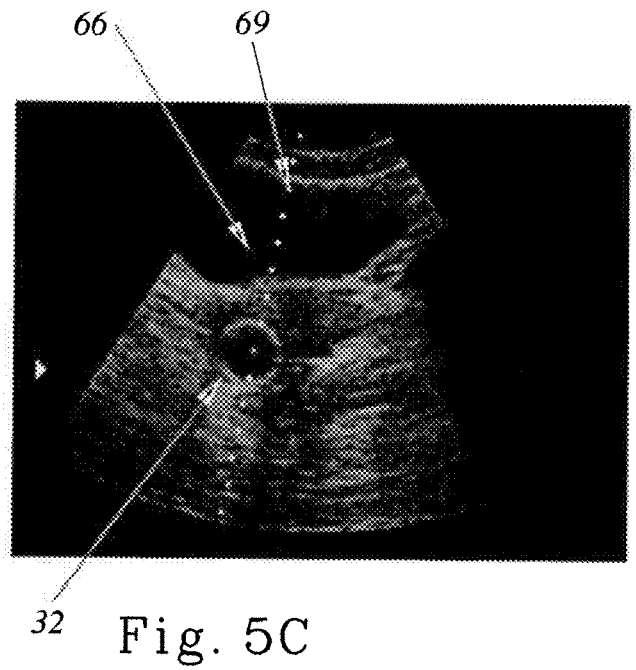
Figure 5D:
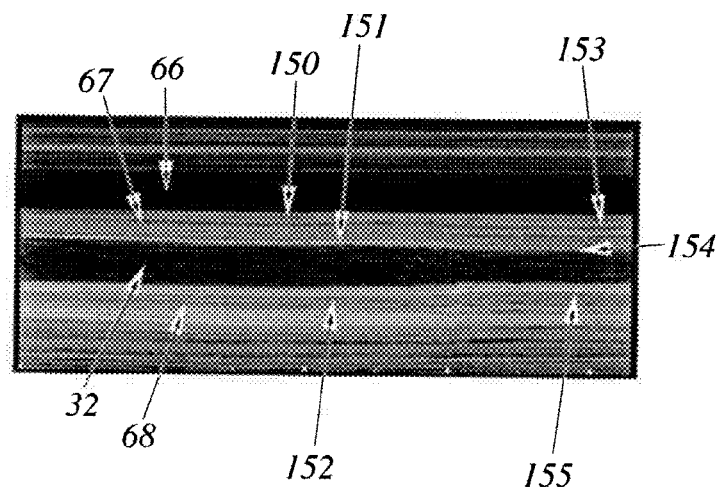

The images shown in FIGS. 5(c) and 5(d) show "quasi-static" tissue strain profiles. The bladder, 66, is a non-echo area (dark) because urine is an acoustically favorable medium. Tissue layers are shown, from which quantitative measurement of deformation of tissue layers can be made. In FIG. 5D, layers 150, 151 and 152 show, respectively, the bladder tissue layer, anterior vaginal tissue layer (vesicovaginal), and posterior vaginal tissue layer (rectovaginal). This particular M-mode image further shows these tissue layers as they move from a strained phase (150, 151, 152) to relaxed phase (153, 154, 155). Movement can be quantified both in distance and rate by reference to the image output of the imaging means, such at that represented in FIG. 5.

The value of visualizing tissue boundary deflection with both B- and M-modes is to permit strain analysis and determine tissue strain, modulus, and other biomechanical properties. B-mode only can be used, but the time to get data is increased because two image sets are required to calculate each increment of strain, for example, the first unstressed position image and the second stressed position images. M-mode permits measurements and data collection as a function of time. Many ultrasound imagers have the capability to show the B- and M-mode at the same screen so the operator understands the scanning path for the M-mode. The dotted lines shown at images of FIGS. 5(a) and 5(c) indicate the scanning path of the corresponding M-mode images. The vertical position on the M-mode image has a geometric correspondence to the anatomical position along the scanning path of the B-mode image. As shown in both of these images, the B-mode ultrasound is directed through inflatable balloon 32 and other tissues of interest adjacent to the balloon in vivo. As the balloon 32 is inflated and deflated by means of operation of the fluid volume controller 50, the M-mode data visualization can show the relative dimensional changes in tissue layers. Using the M-mode visualization of dimensional changes strain can be calculated for imaged tissues and organs.

One method of determining strain levels can be understood with reference to FIG. 5(b) in which three different connective tissue layers are measured over time to obtain normal strain during periodic inflation and dilation of an inflatable balloon 32. The vesicovaginal tissue layer is identified as layer 67 and is between the vagina (in which inflatable balloon 32 is lodged), and the bladder 66. The rectovaginal tissue layer 68 is between the vagina and the rectum (not identified). Identification of these tissues is achieved by comparing the geometric location of each layer at the B-mode image, in this case as shown in FIG. 5(a). The periodic trace 175 superimposed over balloon 32 in the M-mode image corresponds to the balloon internal pressure profile.

Figure 12:
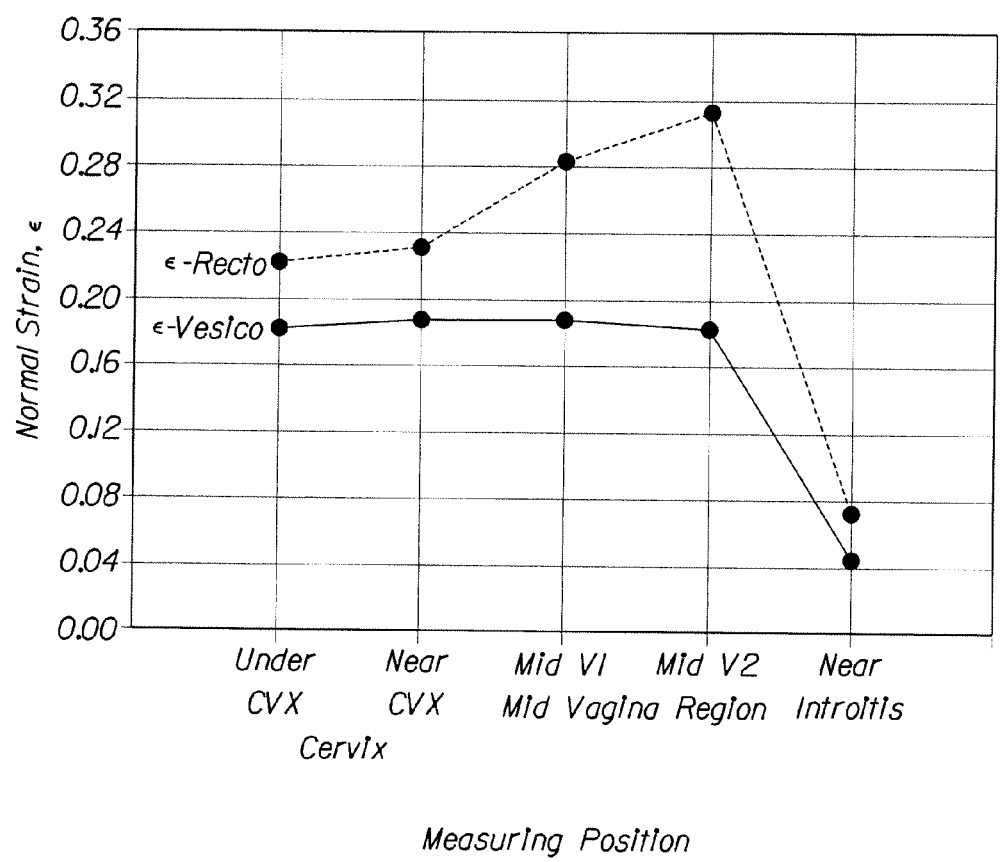
FIG. 12 is the typical strain level varying for different measurement locations which correlate to those indicated in FIG. 1(b).

As shown in FIG. 5(b), when the internal pressure of inflatable balloon 32 increases, the thickness of the adjacent tissue layers decreases. The actual dimensional change of tissue thickness can be obtained by scaling the electronic ruler available from the ultrasound imager and shown as overlapped in the ultrasound image to the number of pixels corresponding to the ruler setting. After calibration, the spatial calibration factor is expressed in units of mm/pixel. Once the vaginal tissue wall boundaries are identified, an image processing program made with MatLab (Mathworks Inc., Natick, Mass.) can acquire the numbers of pixels in a deformation and can calculate the deformation depth in mm. Once deformation values for vesicovaginal and rectovaginal tissue layers are obtained, the local axial strain can be calculated from the formula of equation (1):

$$\varepsilon_z = \frac{(L_{DB} - L_{IB})}{L_{DB}} \qquad (1)$$

where the $\varepsilon_z$ is the axial local strain of the vaginal tissue layers; $L_{DB}$ and $L_{IB}$ are the tissue layer thickness profiles when the balloon is deflated and inflated states. In FIG. 5B, the strain of the vesicovaginal tissue layer is calculated at one location to be 0.22 and the strain of the rectovaginal tissue is calculated as 0.78. It has been found that strain can vary at different parts of the same organ. For example, strain of tissues at different portions of the vagina can vary as shown in FIG. 12.

Another method for determining strain is illustrated with respect to FIGS. 5(c) and 5(d). As shown in FIG. 5(d), the rectangular-shaped strain boxes generated by a MatLab program can be superimposed over tissue layers. While the size of the box can be somewhat arbitrary, one skilled in the art will see that the height of the box should correlate to the thickness of the layer to be measured. FIG. 5(d) shows the bladder wall tissue before strain 150 and after strain 153; the vesicovaginal tissue before strain 151 and after strain 154; and, the rectovaginal tissue layer before strain 152 and after strain 155. By calculating the number of pixels along line 69 in FIG. 5(c) for each respective layer of tissue, a pixel conversion ratio (mm/pixel) can be used to compare the pixel resolution with the number of pixels in the vertical axis of the various strain boxes in FIG. 5(d). The pixel-to-mm conversion permits the dimensional changes in the tissue layers to be reported in mm. Strain can be calculated based on either pixels or mm dimensions. In one embodiment of the method, the size of each pixel is very small (usually less than 33 microns in case of Voluson 730 ultrasound imager for abdominal imaging) compared to the tissue thickness dimension (mm order). Therefore, the tissue dimension measurement error due to the pixel quantization is believed to be negligible. For the tissues imaged in FIG. 5(d), the strain profiles are shown in Table 1.

Figure 6:
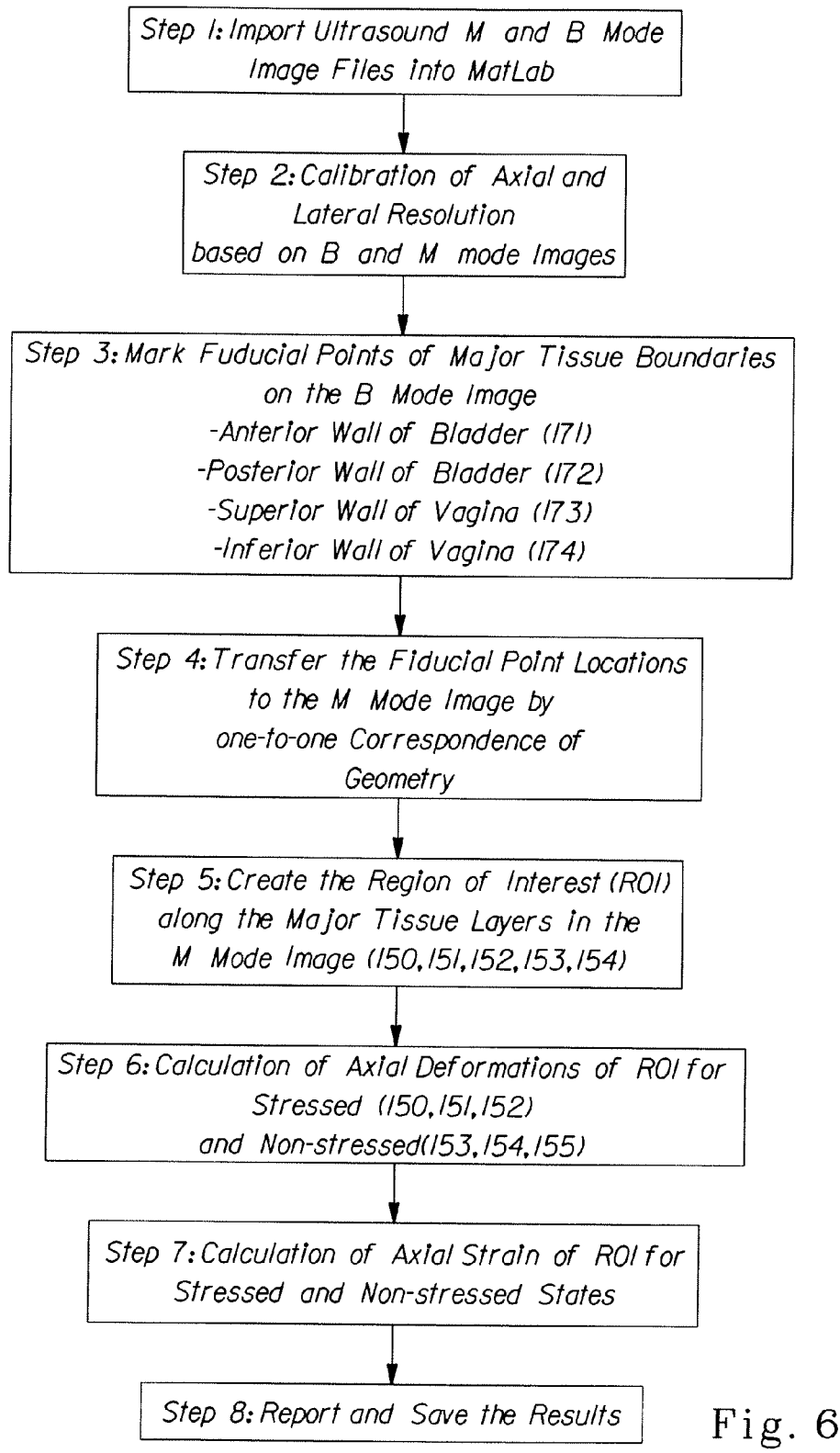
FIG. 6 is a one embodiment of ultrasound image processing using MatLab for the calculation of axial strain.

Tissue deformation and axial strain analysis can be made by computer analysis. In one embodiment, a MatLab® program to analyze the tissue properties of vaginal tissue was run according to the flowchart shown in FIG. 6. The raw image files of ultrasound B and M modes are read into the MatLab® platform; appropriate image file format conversion is necessary for this step such as from DICOM to JPEG or BMP files. With numbers of pixels across the axial depth and lateral width dimension of ultrasound image as shown at FIG. 5, calibration is done for the calculation of mm per pixel. Once this calibration is done, the MatLab® program can calculate the actual dimension from the images of ultrasound or any other imaging modalities. The next step is to take the major points of interest from the B mode image; in case of images shown at FIG. 5, we can see the lower pelvic floor organs. In one application of image analysis, we use the bladder and the vagina as major organs for the strain analysis, for example, as shown in FIG. 5(b), the anterior bladder wall 171, posterior bladder wall, 172, superior vaginal wall, 173, and inferior vaginal wall, 174. These anatomical 'fiducial" points are important to further classify tissue layers such as vesicovaginal and rectovaginal tissues. The MatLab® program can recognize these points on the B mode image and can find the matching locations within the M mode for the strain analysis and recognition of other tissue layers. After these fiducial points are determined, the program allows a user to choose the region of interest (ROI) for the strain measurement. These ROIs should include tissue layers stressed and relaxed (mildly stressed) by the inserted tissue strain device, 30, in this case, a balloon 32. In FIG. 5(d), regions 150, 151, 152 are stressed inferior bladder wall layer, superior vaginal tissue layer, and inferior vaginal tissue layer, respectively. Similarly, the regions 153, 154, 155 correspond to the relaxed tissue layers. The MatLab® program recognizes those ROIs and calculates the strain of each layers with equation (1); in this case three layers of bladder inferior, vaginal superior and inferior walls. In steps 6 and 7 in FIG. 6, the pixel conversion factor obtained in step 2 is used to obtain the metric unit (e.g., millimeter) based tissue layer thickness. As a final step, the program can save the input dialogue parameters such as file name, directory path, etc., and print the calculated strain values on the default output device, e.g., computer monitor screen and/or spreadsheet format output file.

Another embodiment of strain analysis could be based on a tissue deflection measurement. For example, a strain analysis program could be designed to track tissue deflection by insertion of a tissue strain device. In one embodiment the tissue strain device could be a balloon 32 or it could be a tampon-like product if measuring vagina tissues. Tissue deflection information is useful not only in understanding the mechanical properties of tissues, but also for validating the interaction between in vivo products and tissue layers, as well as virtual tissue models.

Figure 7A:
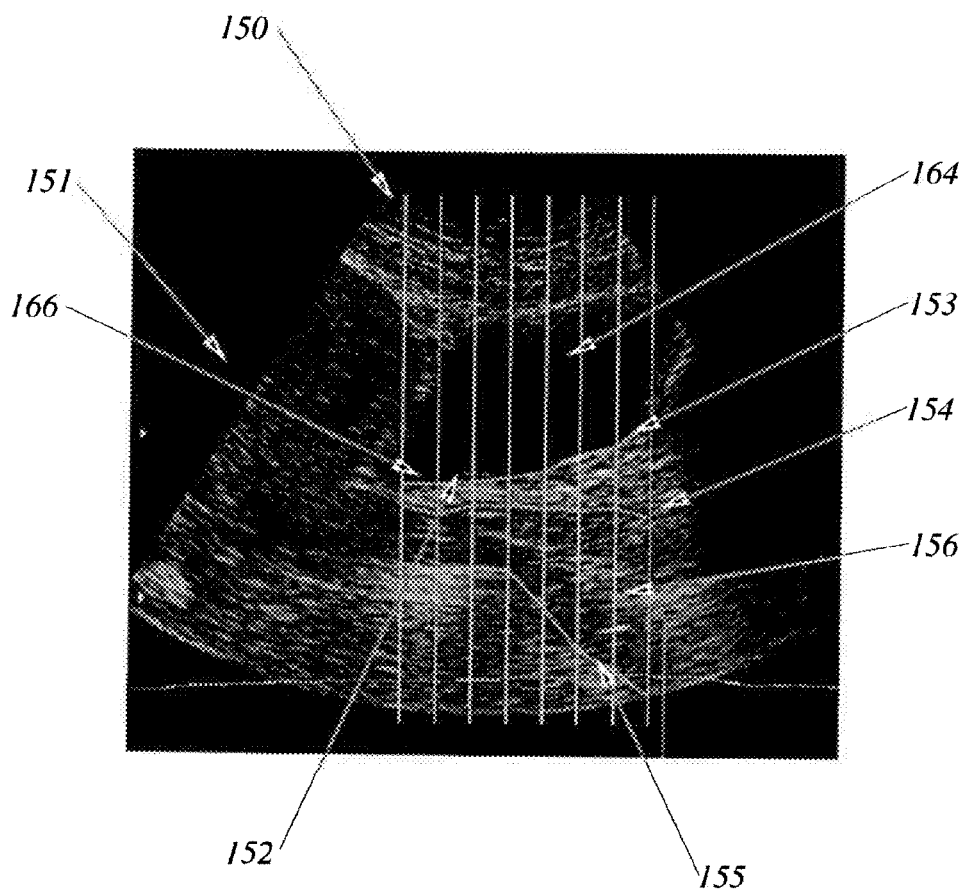
FIG. 7 is a one embodiment of the strain measurement based on the image processing of a ultrasound B-Cine mode.

FIG. 7 shows one example of image analysis for tissue deflection measurement. Specifically, an ultrasound image shows how an object, such as an inserted balloon or tampon applicator can deflect vaginal tissue layers. In FIG. 7(a), a tampon applicator tip is shown inserted into a vagina. The surrounding organs like the bladder posterior wall boundary 153, the superior vaginal tissue layer 154, and rectovaginal tissue layer 155 are visible. A MatLab® program following the flowchart in FIG. 8 can provide tissue deflection analysis for the data shown at FIG. 7. The MatLab® program can generate the tissue boundary tracking lines 153, 154, and 155 of FIG. 7 along the three major layers, and the reference deflection lines 150 for the desired number of measurement positions; in the cases shown in FIG. 7, eight positions on the mid-sagittal plane. The program acquires multiple frames of ultrasound cine mode images and checks the shift in the cross points of tissue tracking lines 153, 154, 155 and the reference deflection lines 150. The tissue tracking lines are built by the program along the boundaries of major organs; those organ boundaries are also changed as an applicator 156 and a balloon 165 are inserted into a vagina. Those reference deflection lines 150 work as local y axis of tissue image, while the reference plane line 166 works as a local x axis. Therefore, the cross-points between the tissue tracking lines and the reference deflection lines indicate the tissue layer deflection at a given position. Finally, the distances from the reference plane line 166 to those cross-points are the tissue deflection data that are saved by the MatLab® program. As the object, such as tampon applicator, is inserted, it is expected that the distance between the superior and the inferior vaginal walls 154 and 155 increases. The cine mode is useful to check the tissue boundary deflection during the insertion process of a balloon or an applicator.

Figure 7B:
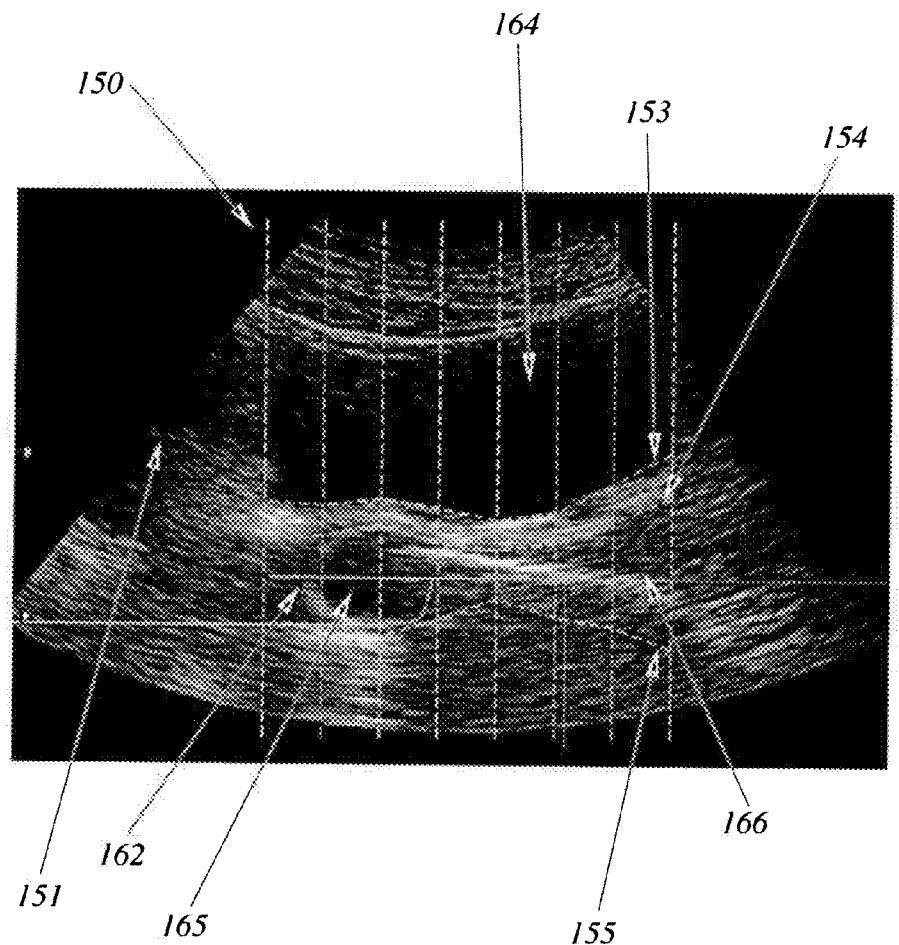
Figure 8:
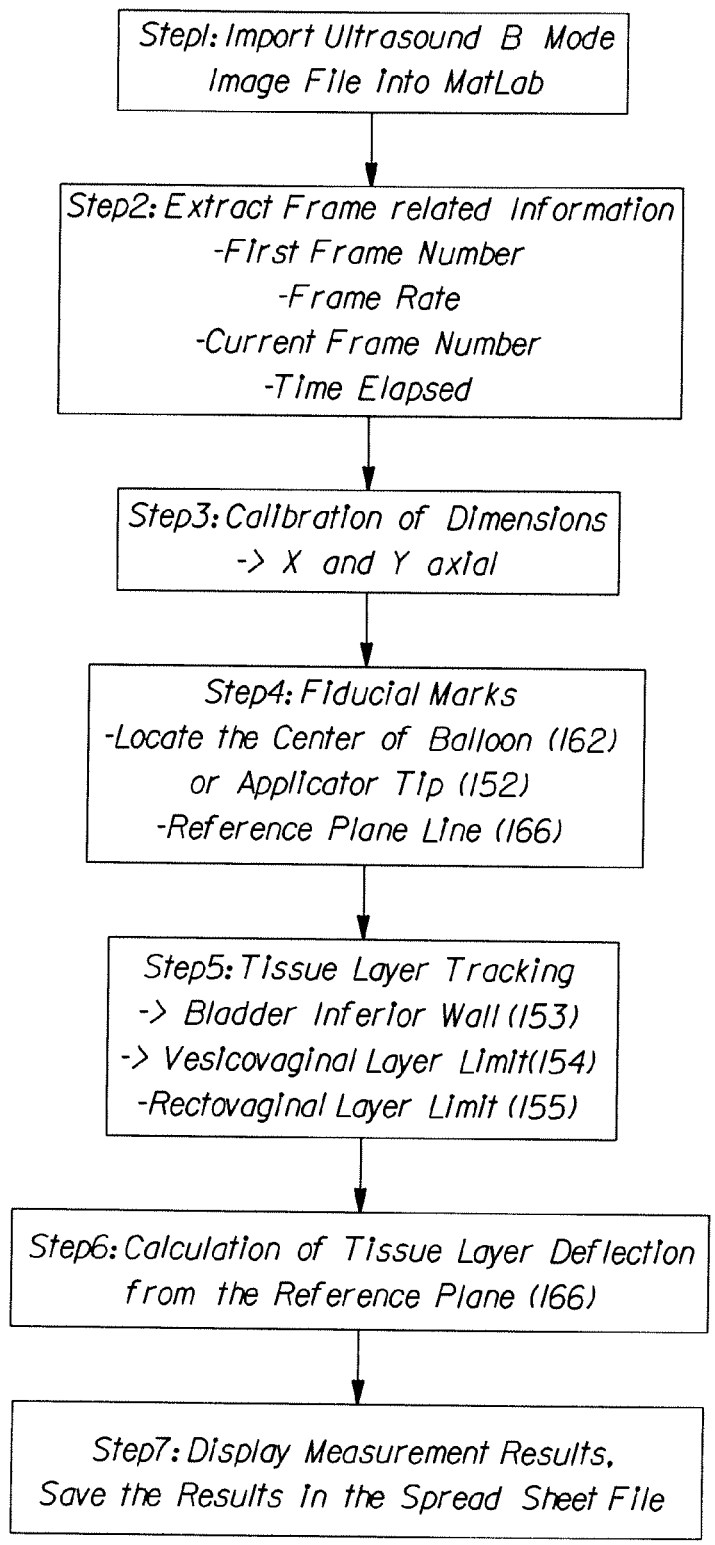
FIG. 8 is a one embodiment of ultrasound B-Cine mode image analysis using MatLab for the strain measurement.

In the image shown in FIG. 7, a part of uterus 151 is also used to determine the onset of reference plane line 166; except the case to measure the tissue deflection under cervix, the reference plane line 166 begins from the near cervix through the near introitus. As shown in FIGS. 7(a) and 7(b), the orientation of an applicator body 156 and balloon tubing 166 could be utilized to find the ending limit of reference plane line 166.

Once the MatLab® program recognizes the starting and ending frames of insertion process (Step 3 in FIG. 8), the program calibrates spatial coordinates along the x and y axis of an image; this calibration process can be as in Step 2 of FIG. 7, so the process generates the calibration factor of mm/pixel. In Step 4, the program recognizes the major fiducial points such as a center of a balloon or an applicator tip, and reference plane line. The program can now builds the evenly-spaced tissue tracking lines 153, 154, 155 over the length of the reference plane line 166. In Step 6, tissue tracking is done and the program recognizes the cross points of the reference deflection lines 150 and tissue tracking lines 153, 154, 155. The program can calculate the normal strain values of tissue layers and saves those results in an output data file.

While strain values are calculated from ultrasound images, pressure values are obtained and recorded by pressure transducer 40 as shown in FIG. 1(a) and related data collection devices such as signal conditioning amplifier 46 and data acquisition module 48. All of the data, including dimensional data from the ultrasound probe 62 can be analyzed by computer 70 to calculate elastic modulus for each tissue or portion of a tissue in which strain is calculated. Pressure level applied on the in vivo inflatable device 30, or balloon 32 can be obtained through the calibration and linear regression analysis.

Figure 9A:
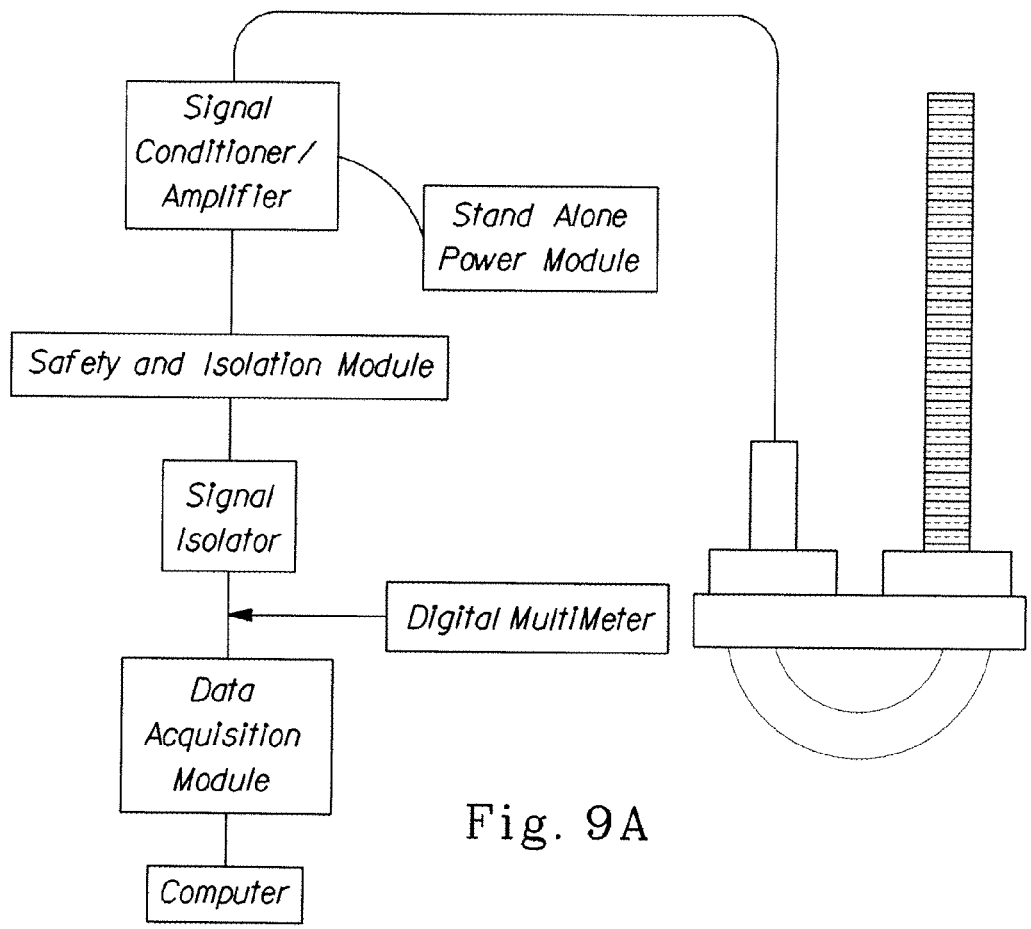
FIG. 9 is the instrumentation scheme for the calibration of pressure transducer, and one typical example of calibration result.

The pressure sensors can be calibrated by the manufacturer and a calibration certificate is usually available with the product. However, because tissue loading pressure can be very low (e.g., less than 1 psi) for soft tissues such as vaginal tissues, it is suggested to calibrate the pressure transducer prior to making measurements with the apparatus of this invention. One method of calibrating the pressure transducer is illustrated in FIG. 9(a). The illustrated method of calibration can be modified according to the types of transducer design and sensor. In one embodiment, the pressure transducer can be a strain-gauge type pressure sensor with electrical insulation between the pressure sensing element and transducer face like the case of physiological pressure transducer. In this type, a liquid column 130 (preferably the same liquid as the one used in the balloon and tissue strain device shown at FIG. 2) stands in vertical section of a U-shaped tube 132. The vertical section of the U-shaped tube has a scale to indicate the height of water column and the U-shaped connecting tube transfers the pressure due to the water column height to the pressure transducer under calibration 131. The signal acquisition and processing instruments can include a signal amplifier 133, a power module 134, a safety and isolation module 135, a signal isolator 136, and data acquisition module 138. These instruments can be identical to the ones used for the in-vivo measurement as described with respect to the apparatus shown in FIG. 1(*a*). Additional data collecting instruments like a digital multimeter 137 (for example, a model 34401A, from Agilent Technologies (Palo Alto, Calif.)) can be used.

The pressure applied on the pressure transducer 131 under calibration is the hydro-head pressure of liquid column 130, which is given as p g h when the p is the density of liquid in the column, g is the gravitational acceleration and h is the height water column. Therefore by adjusting the height of liquid column, the calibration pressure can be changed. Care should be taken to give enough time for each measurement if the transducer has a thermal constant. This calibration procedure can provide an accurate and highly linear calibration as illustrated by the graph shown at FIG. 9(*b*). If the thermal constant effect of a pressure transducer is negligible, a more accurate and fast calibration method can be used, such as that of the calibration unit from Fluke (Everett, Wash.); model 744, Documenting Process Calibration, model 700PD7 Pressure Module, and model 700 PTP Pneumatic Test Pump.

Figure 9B:
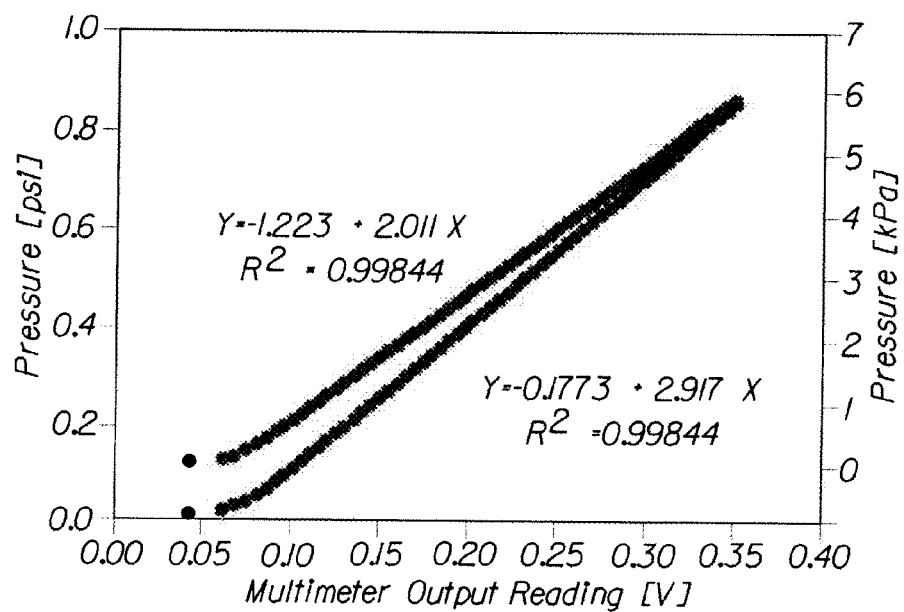
Figure 10:
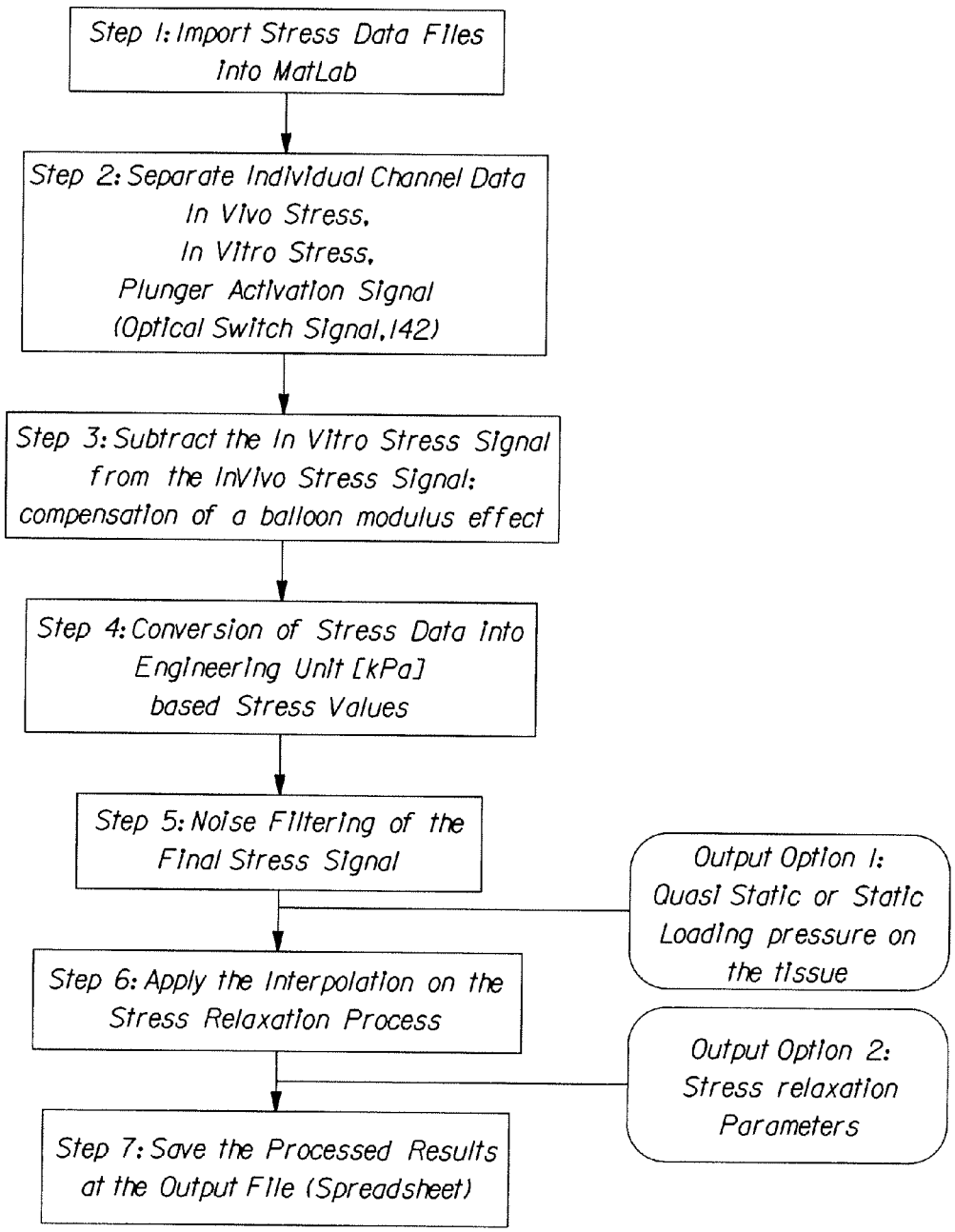
FIG. 10 is a one embodiment of a signal analysis using MatLab for the measurement of in vivo tissue loading stress.

Once calibration of the pressure transducer is achieved, the system 10 can be used to measure in vitro and in vivo pressure. As described above, the net loading pressure applied on a tissue is obtained by subtracting the in vitro balloon pressure from the in vivo total pressure. A flow chart for a MatLab®-based program to handle this stress signal processing is shown at FIG. 10. The program first imports the raw data file of tissue loading pressure measured in vivo. In Step 3 in FIG. 10, the program separates channels of in-vivo and in-vitro pressure transducer signals and optical switch (92 of FIG. 3(*a*)) generates a signal indicating the moment when the manual pushing plate 101 is stopped by the limiter arm 99. This signal means that the full injection of liquid volume into a balloon is done. In the next step, the balloon modulus effect on the pressure signal is compensated; the in vivo pressure signal is subtracted from the in vitro pressure signal, so the net change of pressure signal by the tissue loading is determined. The pressure signal is still a raw data of electrical signal from the transducer, therefore, in Step 4, the program converts the voltage signal into engineering unit based data such as kilo Pascal, kPa [1 Pascal=N/m$^2$, 1 kPa=10$^3$ Pa. The calibration factors found in the pressure transducer calibration as discussed with reference to FIG. 9 are used to convert the voltage signal into the kilo Pascal data. The signal could be still noisy; the signal frequency is in general low considering the viscoelastic property of vaginal tissue; therefore, a low pass filter of unity gain at pass band is applied on the signal. Typical cutoff frequency is as low as 100 Hz, however, depending on the tissue of interest and estimated modulus, this cutoff frequency can be chosen differently. The outcomes of stress signal processing include (1) quasi-static or static loading pressure applied on the tissue layers, and (2) stress relaxation process monitored by the decreasing loading pressure. In the steps 5 and 6, those data become available; the detail of this method is described below in conjunction with FIG. 11.

The noise-filtered stress signal is interpolated to the equation of stress relaxation-exponential decay using parameters such as initial stress, final stress, and decay constant, and these parameters can be used to understand the viscous property of a tissue. The concept of signal processing to calculate those parameters is shown graphically in FIG. 11(*a*); it corresponds to the use of the apparatus as shown in FIGS. 2 and 3. When the syringe pushing handle 101 is pushed to a preset position (volume reduction of syringe), optical switch 92 (if used) detects the moment when the balloon in-vivo is fully expanded and generates a time-stamping signal 142. The pressure level within the in vivo balloon reaches its highest level just before the syringe pushing handle is pushed to the preset position, and the pressure rapidly drops to its initial level 141. This is the moment when the syringe pushing handle is completely stopped, and the transient dynamic pressure starts declining; this transitional pressure effect is mainly caused by turbulent flow of liquid inside tubing line. This transient phenomenon is an artifact of the signal linked to stress relaxation. Therefore, in the signal processing, the initial pressure level and the onset of real stress relaxation are connected linearly 143, as shown graphically in FIG. 11(*b*). The transition between the two pressure levels can be non-linearly made, but the difference in the viscous property related parameters between the linear and non-linear connection was small for the highly elastic in-vivo tissue.

Once the two data points are connected, a three-parameter exponential regression of the format, $A+B\ e^{-Ct}$, can be applied to the processed signal profile. The resulting profile 144 following the equation of relaxation is given at FIG. 11(*b*). Once the tissue loading stress is obtained, further material properties can be available; shear and normal modulus. Table 1 below shows the some of the parameters available from this analysis with respect to a subject vaginal tissue. The strain data shown in Table 1 is used with the stress data analyzed for the modulus data. In Table 1, the measurement of strain by ultrasound images and stress measurement by an in-vivo balloon have been done at each of the four different locations within the middle portion of a vaginal path.

TABLE 1

Viscoelastic parameters available from the strain and stress measurement.

| | Locations within Middle of Vaginal Path | | | | | | | |
|---|---|---|---|---|---|---|---|---|
| | 1 | | 2 | | 3 | | 4 | |
| Parameter | Vesico | Recto | Vesico | Recto | Vesico | Recto | Vesico | Recto |
| Poisson Ratio, $\tau$ | 0.49 | 0.49 | 0.49 | 0.49 | 0.49 | 0.49 | 0.49 | 0.49 |
| Normal Strain, $\epsilon$ | 0.5 | 0.435 | 0.433 | 0.375 | 0.533 | 0.308 | 0.141 | 0.256 |
| Normal Short Term Stress [kPa], $\sigma_o$ | 7.650 | 7.650 | 7.212 | 7.212 | 7.440 | 7.440 | 8.995 | 8.995 |
| Normal Long Term Stress [kPa], $\sigma_\infty$ | 7.065 | 7.065 | 6.972 | 6.972 | 7.223 | 7.223 | 8.192 | 8.192 |
| Shear Decay Constant [s$^{-1}$], $\beta$ | 0.059 | 0.059 | 0.241 | 0.241 | 0.2 | 0.2 | 0.058 | 0.058 |
| Relaxation Time [s], $\tau_\epsilon$ | 16.949 | 16.949 | 4.149 | 4.149 | 5.000 | 5.000 | 17.241 | 17.241 |

TABLE 1-continued

Viscoelastic parameters available from the strain and stress measurement.

| | Locations within Middle of Vaginal Path | | | | | | | |
|---|---|---|---|---|---|---|---|---|
| | 1 | | 2 | | 3 | | 4 | |
| Parameter | Vesico | Recto | Vesico | Recto | Vesico | Recto | Vesico | Recto |
| Short Term Shear Modulus [kPa], $G_o$ | 5.1342 | 5.9014 | 5.5892 | 6.4537 | 4.6841 | 8.1060 | 21.4075 | 11.7908 |
| Long Term Shear Modulus [kPa], $G_\infty$ | 4.7416 | 5.4501 | 5.4032 | 6.2389 | 4.5475 | 7.8696 | 19.4964 | 10.7383 |
| Elastic Bulk Modulus* [kPa], K | 235.50 | 270.69 | 268.36 | 309.87 | 225.86 | 390.85 | 968.32 | 533.33 |

By measuring parameters such as normal strain, σ and stress, ε, we can obtain the secondary parameters, which are important to understand the biomechanical behavior of in vivo tissues. For example, shear modulus, G, with Poisson ratio, ν, is calculated from the equation of $$G = \frac{E}{2(1+v)} = \frac{\sigma/\varepsilon}{2(1+v)} \quad (2)$$

where E is Young's modulus. The elastic bulk modulus, K, is obtained by $$K = \frac{E}{3(1-2v)} \quad (3)$$

Viscoelastic properties can be derived from the stress relaxation process, which is described as an instantaneous shear modulus, $$G(t) = \frac{\sigma(t)}{\varepsilon \cdot 2(1+v)} \quad (4)$$

where the time-dependent stress relaxation process is σ(t) for the given constant strain, ε. This shear modulus is described by the following general format of equation, $$G(t) = G_\infty + (G_o - G_\infty)e^{-\beta t} \quad (5)$$

where $G_o$ is the short term shear modulus, $G_\infty$ is the long term shear modulus, and β is the shear decay constant.

FIG. 12 shows one typical graphical result showing the non-uniform distribution of normal strain in a human tissue, in this case, vaginal tissue layers. The graph shows the trend of declining strain of both vesicovaginal and rectovaginal tissue layers at the cervix and near introitus. The rectovaginal tissue layer tends to deform more than the vesicovaginal tissue layers, which could indicate the relative effects of surrounding organs-bladder and rectum. This graph suggests that the strain distribution of an in-vivo tissue layer can be locally determined.

Figure 13:
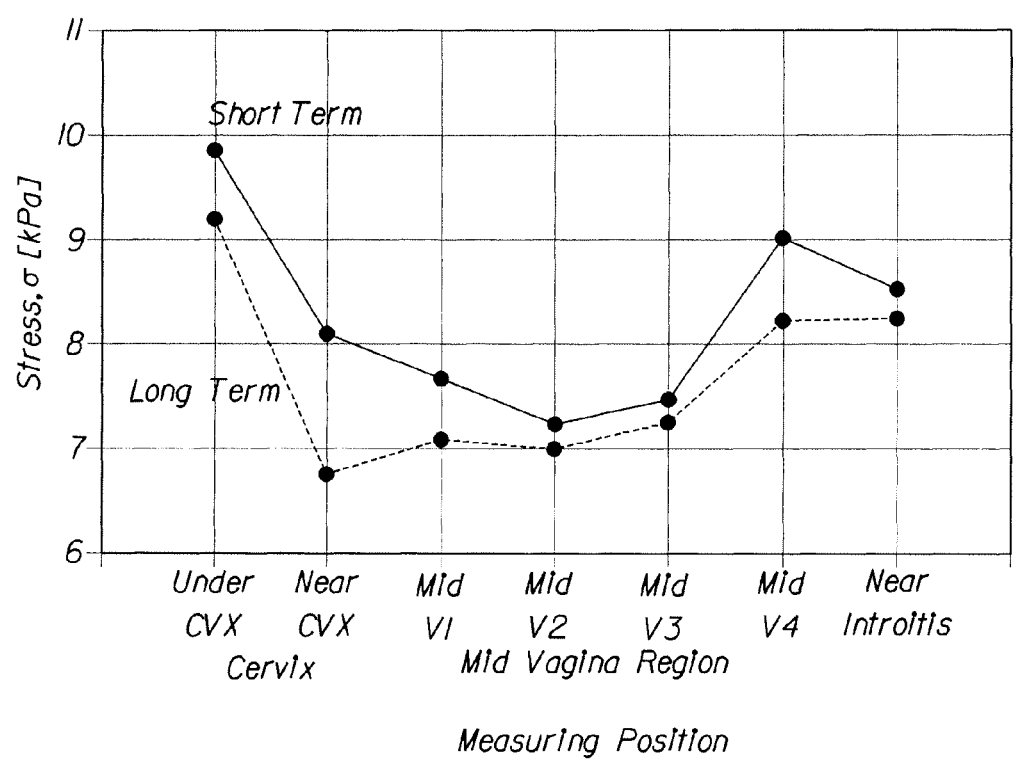
FIG. 13 is the typical long term and short term stress levels varying for different measurement locations which correlate to those indicated in FIG. 1(b).

FIG. 13 shows viscosity related properties of an in vivo tissue including initial and final stress levels that the tissue experiences. As the graph shows, the mid portion of a vagina can experience a low level of short and long term stress to a given constant strain, and as the measuring position moves away from the mid portion, the stress tends to increase, which implicates different compositions of vaginal tissue layer and as a result, different biomechanical properties of tissue at different locations of vagina.

Method to Determine Biomechanical Properties of Internal Tissues Using Inverse Finite Element Analysis The device of the present invention can be used to determine the biomechanical properties of internal tissues by a methodology referred to herein as "inverse finite element analysis" (hereinafter referred as "inverse FEA"). Inverse FEA is a numerical approach where unknown input parameters are determined such that simulated experiment results with a finite element analysis method (hereinafter referred as "FEA") match actual experiment results.

The first step in the Inverse FEA method is to construct a numerical model for the expandable tissue strain device 30 using measured in-vitro properties of the expandable tissue strain device 30. Next, a numerical model for the body 12 can be constructed which includes tissues and/or organs, and the body cavity of interest characterized with certain numerical equations (i.e., material models) comprising arbitrary parameters in the equations, and certain boundary conditions. The third step involves numerically simulating the controlled volume change of the expandable tissue strain device 30, which is inserted into the body cavity to a certain point and obtaining the simulation results including the change in pressure of the expandable tissue strain device 30 and the change in position or dimension of the tissues or organs of interest. Step four involves comparing the simulated results from Step 3 with the equivalent measured in-vivo results from the use of device 10 of the present invention, i.e., the change in pressure of the expandable tissue strain device 30 measured by the external pressure transducer 40, and the change in position or dimension of the tissues or organs of interest measured by the external imaging device 60.

If Step 4 of the Inverse FEA method does not result in agreement between the simulated results and the equivalent measured in-vivo results, return to Step 2, change the parameters in the material models, and then iterate Step 3 and 4. This process can continue until the simulated results agree with the equivalent measured in-vivo results with desired accuracy. Once the agreement is achieved, the biomechanical properties of the tissues or organs of interest are finally determined in the form of the material models comprising the optimized parameters.

Any of known software, algorithms, numerical codes, or numerical solvers can be use for the inverse FEA of the present invention. Such tools may give explicit solutions or implicit solutions. Preferably, such tools are capable of solving the equations of motion using an explicit time integration technique that incorporates lumped mass matrices and vectorization/parallelization algorithms. This type of numerical solver is available as any commercial explicit FEA software package such as ABAQUS/Explicit® from Abaqus, Inc. of Providence, R.I., LS-DYNA® from Livermore Software Technology Corp. of Livermore, Calif., and ANSYS LS-DYNA® from Ansys Inc. of Cannonsburg, Pa. Unless otherwise mentioned, LS-DYNA® is used as the numerical code for the inverse FEA of the present invention.

Constructing a numerical model for the expandable tissue strain device 30 requires characterization of any in-vitro (i.e., measured externally to the body) mechanical behavior of the expandable tissue strain device 30. In one embodiment, characterization can be achieved by measuring the pressure change read by the pressure transducer 40, to which the expandable tissue strain device 30 is connected via the tubing 42, in accordance with the controlled volume change of the expandable tissue strain device 30 by the fluid volume controller 50, being placed in free air (e.g., being held by hand at the joint between the expandable tissue strain device 30 and the tubing 42 in the exterior to the body).

Figure 14:
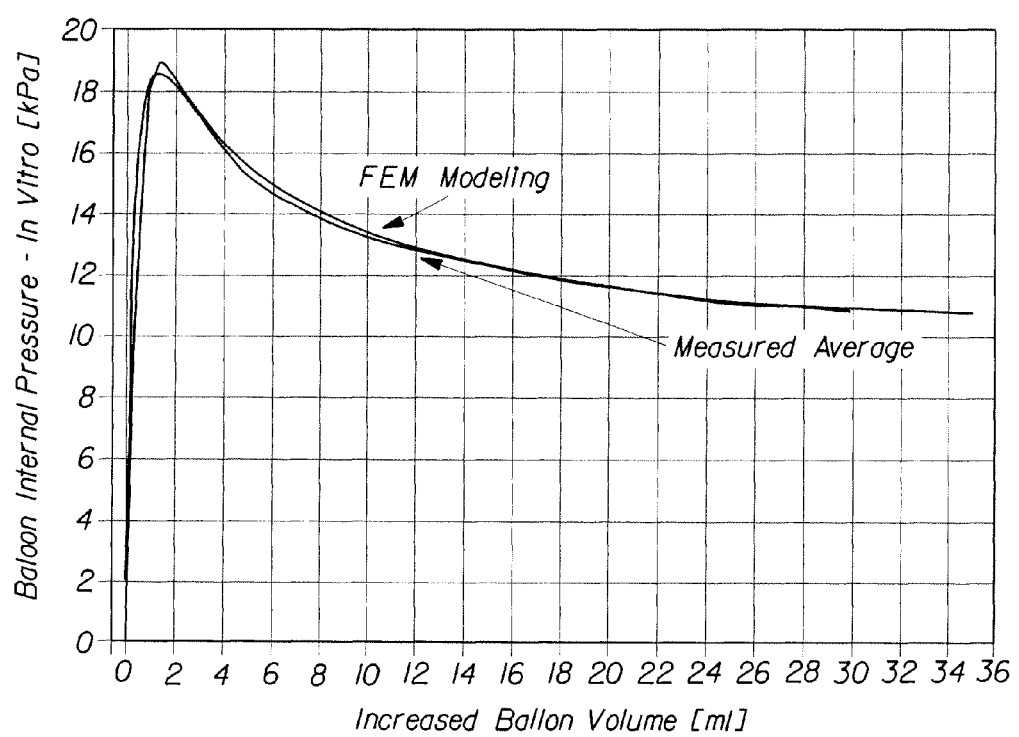
FIG. 14 is a graph showing a relationship between the pressure change measured by the pressure transducer of the present invention and the volume change of the expandable tissue strain device of the present invention.

Solid line 211 in the graph of FIG. 14 (labeled "Measured Average) illustrates a relationship between the pressure change measured by the pressure transducer 40 and the volume change of the expandable tissue strain device 30 controlled as the fluid injection volume from the fluid volume controller 50, for one embodiment where the expandable tissue strain device 30 is an inflatable latex balloon as described above. The numerical model for the expandable tissue strain device 30 may comprise any type of finite elements defined by any type of element formulations. In one embodiment, where the expandable tissue strain device 30 is the inflatable latex balloon hereinabove, shell elements (set with LS-DYNA syntax: *ELEMENT_SHELL) with the Belytscho-Tsay formulation (set with LS-DYNA syntax: * SECTION_SHELL including a variable setting: ELFORM=2) may be used. The numerical model for the expandable tissue strain device 30 may also comprise any type of material models. In one embodiment, where the expandable tissue strain device 30 is the inflatable latex balloon hereinabove, the Mooney-Rivlin hyperelastic rubber model (set with LS-DYNA syntax: *MAT_MOONEY-RIVLIN_RUBBER) may be used.

A dashed line 212 in the graph of FIG. 14 (labeled "FEM Modeling") illustrates a simulated relationship between the pressure change and the volume change of the expandable tissue strain device 30 for one embodiment, where the expandable tissue strain device 30 is the inflatable latex balloon described above, showing agreement with the measured relationship between the pressure change and the volume change of the expandable tissue strain device 30.

Construction of a numerical model for the body 12 which includes the tissues or organs, and the body cavity of interest may be composed of imaging of the anatomy of the part of the body including the tissues or organs and the body cavity of interest, followed by numerical reconstruction of the part of the body, segmentation for the tissues or organs, rendering of the reconstructed/segmented part of the body to finite elements (i.e., "meshing"), and then, assignment of certain material models comprising arbitrary parameters to the segmented parts for the tissues or organs of interest and setting of certain boundary conditions. Methods for such imaging are included in co-pending, commonly assigned U.S. patent applications Ser. Nos. 11/071916 and 11/071918 to Anast et al., and 11/071920 and 11/072152 to Macura et al.

The imaging of the anatomy of the part of the body including the tissues or organs and the body cavity of interest may be achieved by any of known imaging devices for imaging a living body including CT scan devices, MRI devices, ultrasound devices, X-ray devices, and the like. In one embodiment, the imaging device is a MRI device, for example, available from GE Healthcare of Waukesha, Wis., under the trade name of Genesis Sigma 1.5 Echo Speed LX. The image taken with the imaging device may comprise a set of images corresponding to a series of cross sections of the part of the body along one or more certain axes, which may be rendered to provide three-dimensional definition of the part of the body by means known in the art.

Numerical reconstruction of the part of the body including the tissues or organs and the body cavity of interest may be achieved by any commercial computer aided design (hereinafter referred as "CAD") software package such as I-DEAS® MasterSeries from UGS Corp. of Plano, Tex., SolidWorks® from SolidWorks Corp. of Concord, Mass., MIMICS® from Materialise Corp. of Ann Arbor, Mich., Geomagic Studio® from the Raindrop Geomagic, Inc. of Research Triangle Park, N.C., Scan IP/FE® from Simpleware Ltd., of United Kingdom, and 3D-DOCTOR® from Able Software Corp. of Lexington, Mass. The numerical reconstruction of the part of the body including the tissues or organs and the body cavity of interest may also be done as part of the MRI scanning and data processing.

The reconstructed part of the body may have a one-dimensional, two-dimensional, or three-dimensional shape. It also may include certain simplifications for efficient computing in the following procedures of the inverse FEA. It may include any added line, area, or volume, which does not exist in the actual image of the body or the actual body. Its boundary may be set to be a boundary of the actual image of the body or the actual body or may be set arbitrarily according to positions, displacements and deformations of the tissues or organs of interest, and for efficient computing in the following procedures of the inverse FEA.

The numerical reconstruction of the part of the body may be alternatively achieved by drawing using certain dimensions taken from the image of the part of the body from the imaging device or the reconstructed part of the body by the CAE package. In this approach, the reconstructed part of the body including the tissues or organs and the body cavity of interest may comprise any regular or irregular shapes of lines, areas, or volumes and the dimensions taken from the image of the part of the body from the imaging device or the reconstructed part of the body by the CAE package are assigned to define the shapes. For efficient computing in the following procedures of the inverse FEA, the reconstructed part of the body including the tissues or organs and the body cavity of interest may also comprise approximation in shapes using simple equations, for example, an ellipse or cylinder, etc.

In one embodiment, where the imaging device is a MRI device and the CAE package is MIMICS® from Materialise Corp. of Ann Arbor, Mich., a set of cross-sectional images of the part of the body from the MRI device may be written in the DICOM format. Such DICOM files comprising the set of cross-sectional images of the part of the body can be exported to MIMICS® and rendered to provide numerical reconstruction of the anatomy of the part of the body.

Segmentation for the tissues or organs in the reconstructed part of the body and meshing may be conducted sequentially or simultaneously using any commercial software package designed for either or both of them. The meshing may follow the segmentation or vice versa. The software package useful may include any of commercial software packages for CAD such as described above, and any of commercial software packages for pre-processing of FEA such as Hypermesh® from Altair Engineering Inc. of Troy, Mich, I-DEAS® from UGS Corp. of Plano, Tex., ABAQUS® from Abaqus Inc. of Providence, R.I., LS-PREPOST® from Livermore Software Technology Corp. of Livermore, Calif., and ANSYS LS-DYNA® from Ansys Inc. of Cannonsburg, Pa. For the meshing, any type of elements can be selected such as tetrahedral and hexahedral solid elements, triangular and quadrilateral shell elements, beam and discrete line elements and concentrated mass elements. Multiple formulations of the selected elements are available to simulate the behavior desired. In one embodiment, where the software package used is MIMICS®, the segmentation for the tissue or organs and the meshing can be done with the same software package as the numerical reconstruction of the part of the body including the tissues or organs and the body cavity of interest, in such a way that instructed in the software package. In another embodiment, the numerical reconstruction of the part of the body including the tissues or organs and the body cavity of interest is done by any CAD software package such as MIMICS® and the reconstructed part of the body is exported to any software package for pre-processing of FEA for following segmentation and meshing such as Hypermesh®.

For the meshing, any type of finite elements defined by any type of element formulations can be selected. The segments for the tissues or organs of interest may have the same elements or different elements. In one embodiment, where the reconstructed part of the body includes the vaginal cavity defined as a cavity between the vesico vaginal tissue and the recto vaginal tissue, and segmented parts corresponding to the vesico vaginal tissue, the recto vaginal tissue, the bladder, the urethra, the uterus including the cervix, the rectum, and the pelvic bone, the vesico vaginal tissue, the recto vaginal tissue, the uterus including the cervix, and the pelvic bone may comprise solid elements (set with a LS-DYNA syntax: *ELEMENT_SOLID), and the bladder, the urethra, and the rectum may comprise shell elements (set with a LS-DYNA syntax: *ELEMENT_SHELL).

Once the reconstructed part of the body including the tissues or organs and the body cavity of interest is rendered to be a model comprising finite elements, certain material models comprising arbitrary parameters are set for the segmented parts for the tissues or organs of interest and certain boundary conditions are provided. Setting material models comprising arbitrary parameters for the segmented parts for the tissues or organs of interest, and setting certain boundary conditions can be achieved by, any commercial software packages for pre-processing for FEA, such as Hypermesh® from Altair Engineering Inc. of Troy, Mich., I-DEAS® from UGS Corp. of Plano, Tex., ABAQUS® from Abaqus Inc. of Providence, R.I., LS-PREPOST® from Livermore Software Technology Corp. of Livermore, Calif., and ANSYS LS-DYNA® from Ansys Inc. of Cannonsburg, Pa, or by manually editing the input files for the model of the part of the body including the tissues or organs and the body cavity of interest.

The material models useful for the inverse FEA of the present invention include rigid body material models (such as set with LS-DYNA syntax: *MAT_RIGID, etc.), elastic material models (such as set with LS-DYNA syntax: * MAT_ELASTIC, etc.), viscoelastic material models (such as set with LS-DYNA syntax: * MAT_VISCOELASTIC, etc.), hyperelastic material models (such as set with LS-DYNA syntax: *MAT_MOONEY-RIVLIN_RUBBER, * MAT_B-LATZ-KO_RUBBER, *MAT_BLATZ-KO_ FOAM, * MAT_OGDEN_RUBBER, *MAT_HYPERELASTI-C_RUBBER, etc.), hyperelastic material models including viscoelasticity, hyperelastic soft tissue material models (such as set with LS-DYNA syntax: *MAT_SOFT_TISSUE) and any other material models available. The material models may also be isotropic, anisotropic, or orthotropic. The boundary conditions may be applied to any node, any point, any element, and/or any segmented part of the finite elements and may include translational constraints, rotational constraints, joints, contacts with certain coefficient of friction values, constant distances, pressures, forces, and the like.

In one embodiment, where the reconstructed part of the body includes the vaginal cavity defined as a cavity between the vesico vaginal tissue and the recto vaginal tissue, and segmented parts corresponding to the vesico vaginal tissue, the recto vaginal tissue, the bladder, the urethra, the uterus including the cervix, the rectum, and the pelvic bone, the vesico vaginal tissue and the recto vaginal tissue may comprise the Blatz-Ko hyperelastic foam model (set with LS-DYNA syntax: *MAT_BLATZ-KO_FOAM), the bladder may comprise the Mooney-Rivlin hyperelastic rubber model (set with LS-DYNA syntax: *MAT_MOONEY-RIVLIN_RUBBER), the urethra may comprise the Blatz-Ko hyperelastic rubber model (set with LS-DYNA syntax: *MAT_B-LATZ-KO_RUBBER), the uterus including the cervix and the rectum may comprise the elastic material model (set with LS-DYNA syntax: *MAT_ELASTIC), and the pelvic bone may comprise the rigid body model (set with LS-DYNA syntax: *MAT_RIGID). In this embodiment, as the boundary conditions, the pelvic bone may comprise translational and rotational constraints in x, y, z directions (set within the code lines for *MAT_RIGID) and nodes on the volume boundary may comprises translational and rotational constraints in x, y, z directions.

In another embodiment, the constitutive equations used to represent the biomechanical response of the various soft tissue regions, including but not limited to the vaginal wall tissues, the bladder wall, the smooth muscle fibers in the urethra, the cervix the uterus, and the pelvic floor, may include point to point description of vector fields to represent local collagen and muscle fiber direction(s). These fiber directions can be incorporated into the hyperelastic material modeling framework to render anisotropy to the behavior of the tissue. Continuum based transversely isotropic single fiber family reinforced hyperelastic models (such as set with LS-DYNA syntax: *MAT_SOFT_TISSUE), or multiple fiber family orthotropic hyperelasticity models (such as disclosed by Haridas B, Weiss J. W., Grood E. S., and Butler D. L.: Orthotropic Hyperelasticity with Two Fiber Families: A Study of the Effect of Fiber Organization on Continuum Mechanical Properties in Soft Tissues, International Symposium on Ligaments and Tendons, U California San Francisco, 2004) implemented through user subroutines for specialized material behavior in ABAQUS® (UMAT) can also be used to simulate more complex anisotropic behavior. Fiber directions in various tissues can be determined by quantitative stereology techniques applied to histology studies on cadaveric tissue as well as from diffusion tensor imaging techniques available in MRI based imaging technology technology. The constitutive equations could also include voluntary or involuntary smooth muscle activation capabilities via implementation of an active element model into the user defined material subroutines in LS-DYNA® and/or ABAQUS®.

Values obtained or estimated from public literature may be used as starting values for the parameters of the material models of the tissues or organs before the inverse FEA of the present invention. For example, the following publications disclose mechanical properties of some skeletal muscles which may be used to set starting values for the parameters of the material models of muscular tissues in pelvic floor muscles: *Passive Transverse Mechanical Properties of skeletal Muscle Under In vivo Compression*, by Bosboom et al., published in the Journal of Biomechanics, 34 (2001) 1356-1368; and *Three-dimensional Finite Element Modeling of Skeletal Muscle Using a Two-domain Approach: Linked Fiber-matrix Mesh Model*, by Yucesoy et al., published in the Journal of Biomechanics, 35 (2002) 1253-1262. Based on information on such publications, for example, skeletal muscles such as the levator ani may include the elastic material model (set with LS-DYNA syntax: *MAT_ELASTIC) with starting Young's modulus value of between 15 kPa and 150 kPa and starting Poisson's ratio value of 0.4.

Approximation of the parameters of the material models for the tissues or organs of interest using in-vivo data on the effect associated with any change in the body may precede the inverse FEA on the use of the device of the present invention inserted into the body. In one embodiment, where the part of the body including the tissues or organs and the body cavity of interest includes the vaginal cavity defined as a cavity between the vesico vaginal tissue and the recto vaginal tissue, the vesico vaginal tissue, the recto vaginal tissue, the bladder, the urethra, the uterus including the cervix, the rectum, and the pelvic bone, such a change in the body may include various states of filling of the bladder and various states of filling of the rectum. When the change of filling of the bladder is selected as the change in the body, the approximation of the parameters of the material models for the tissues or organs of interest can be achieved, by, using any imaging device, imaging the anatomy of the part of the body at different states of filling of the bladder, followed by inverse FEA until simulated positions and dimensions of the tissues and organs in the part of the body approximate the actual positions, dimensions thereof from the actual images at different volumes of the bladder corresponding the different states of filling volumes and intravesicle pressures within the bladder. Vesicle pressures can be easily measured during above said experiments via transurethral placement of a microcatheter based pressure transducer in the bladder vesicle.

Another example of the change in the body may include various positions of the subject (e.g., standing, leaning over, sitting lying, etc.). The approximation of the parameters of the material models for the tissues or organs of interest can be achieved by, using any imaging device which allows different positions of the subject such as an open MRI device, for example, available from Fonar Corp. of Melville, N.Y., under the trade name of Upright® MRI 0.6 T, imaging the anatomy of the part of the body with different positions of the subject, followed by inverse FEA until simulated positions and dimensions of the tissues and organs in the part of the body approximate the actual positions and dimensions thereof from the actual images taken by the imaging device over different positions of the subject.

Once the numerical model for the expandable tissue strain device 30 and the part of the body 12 including the tissues or organs, and the body cavity of interest are constructed, the numerical simulation may be conducted, where the numerical model of the expandable tissue strain device is placed in the body cavity of the numerical model of the part of the body at the same position as in the actual in-vivo measurement with the device of the present invention and the numerical model of the expandable tissue strain device is inflated up to the same volume as in the actual in-vivo measurement with the device of the present invention. This numerical simulation can be done by any known FEA code. Once processing of the simulation is completed, the simulation results may be obtained using any appropriate software package for post-processing for FEA such as ABAQUS® Viewer from Abaqus Inc. of Providence, R.I., LS-PREPOST® from Livermore Software Technology Corp. of Livermore, Calif., Hyperview® from Altair Engineering Inc. of Troy, Mich., EnSight® from Computational Engineering International of Apex, N.C., ANSYS LS-DYNA® from Ansys Inc. of Cannonsburg, Pa.

In one embodiment, where the FEA code is LS-DYNA®, LS-PREPOST® from Livermore Software Technology Corp. of Livermore, Calif., or Hyperview® from Altair Engineering Inc. of Troy, Mich., can be used for the post-processing. The simulation results are subjected to qualitative and/or quantitative comparison with the actual in-vivo measurement results under the comparable test conditions (The actual in-vivo measurement test conditions may be obtained by synchronizing the pressures and volumes of the expandable tissue strain device to the B-mode ultrasound signal in time in one embodiment where the external imaging device 60 is an ultrasound device available from Medison-GE Healthcare of Waukesha, Wis.)

In one embodiment, the simulation results and the actual in-vitro measurement results are compared in terms of the quantities including the change in pressure of the expandable tissue strain device and the change in position or dimension of the tissues or organs of interest. The change in position or dimension of the tissues or organs of interest may be compared by projecting or superimposing the simulated images of the tissues or organs on the actual images thereof taken by the imaging device of the present invention. Alternatively, the change in position or dimension of the tissues or organs of interest may be compared by comparing certain dimensions defining the tissues or organs of interest taken from the simulation results and from the corresponding actual images of the tissues or organs.

If the qualitative and/or quantitative comparison between the simulated results and the actual results does not reach agreement within desired accuracy, adjust the parameters in the material models and then iterate the simulation and the comparison between the simulated results and the actual results until the simulated results match the actual results within desired accuracy. Once the agreement is achieved, the biomechanical properties of the tissues or organs of interest are finally determined in the form of the material models comprising the optimized parameters.

In one embodiment, where the part of the body including the tissue or organs of interest includes the vaginal cavity defined as a cavity between the vesico vaginal tissue and the recto vaginal tissue, the vesico vaginal tissue comprising the Blatz-Ko hyperelastic foam model (set with LS-DYNA syntax: *MAT_BLATZ-KO_FOAM), the recto vaginal tissue comprising the Blatz-Ko hyperelastic foam model (set with LS-DYNA syntax: *MAT_BLATZ-KO_FOAM), the bladder comprising the Mooney-Rivlin hyperelastic rubber model (set with LS-DYNA syntax: *MAT_MOONEY-RIVLIN_RUBBER), the urethra comprising the Blatz-Ko hyperelastic rubber model (set with LS-DYNA syntax: *MAT_BLATZ-KO_RUBBER), the uterus including the cervix comprising the elastic material model (set with LS-DYNA syntax: *MAT_ELASTIC), the rectum comprising the elastic material model (set with LS-DYNA syntax: *MAT_ELASTIC), and the pelvic bone comprising the rigid body model (set with LS-DYNA syntax: *MAT_RIGID), the parameters in the material models are finally defined in the format of LS-DYNA input files, as Table 2 below.

TABLE 1

Material Model Parameters for LS-DYNA (Units: mm - mg - sec)

| | Variable # | | | | | | |
|---|---|---|---|---|---|---|---|
| | 2 | 3 | 4 | 5 | 6 | 7 | 8 |
| Vesico vaginal tissue | 0.100e−08 | 0.00250 | | | | | |
| Recto vaginal tissue | 0.100e−08 | 0.00125 | | | | | |
| Bladder | 0.100e−08 | 0.4990 | 0.0075 | 0.00250 | | | |
| Urethra | 0.100e−08 | 0.1000 | | | | | |
| Uterus and cervix | 0.200e−08 | 0.0500 | 0.2000 | | | | |
| Rectum | 0.400e−08 | 0.9000 | 0.3500 | | | | |

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What we claim is:

1. A computational model for describing physical interactions between a human vagina and cervix and a device placed into said vagina, said model being a computer-based virtual environment, said model comprising defined material parameters and boundary conditions for tissues of said vagina and said cervix, said model computing output parameters being the result of virtual simulations of physical interactions of said device and said vagina and said cervix.

2. The computational model of claim 1, wherein said virtual simulations include simulations of physical interactions relating to insertion, deformation, relocation, or removal of said device.

3. The computation model of claim 1, wherein said device is chosen from the group consisting of absorbent devices and nonabsorbent devices.

4. The computational model of claim 3, wherein said absorbent devices are selected from the group consisting of absorbent pessaries, vaginal swabs, tampons, and tampon applicators.

5. The computational model of claim 3, wherein said nonabsorbent device is a surgical instrument.

6. The computational model of claim 3, wherein said nonabsorbent devices are selected from the group consisting of nonabsorbent pessaries, rings, catheters, balloons, and female condoms.

7. A computational model for describing physical interactions between a human pelvic environment and a penetrating device placed into the pelvic environment, said model being a computer-based virtual environment, said model comprising defined material parameters and boundary conditions for tissues of the pelvic environment, said model computing output parameters being the result of virtual simulations of physical interactions of said penetrating device and said pelvic environment.

8. The computational model of claim 7, wherein said penetrating device is absorbent and selected from the group consisting of pessaries, vaginal swabs, tampons, and tampon applicators.

9. The computational model of claim 7, wherein said penetrating device is nonabsorbent and selected from the group consisting of pessaries, surgical instruments, blunt objects, and tampon applicators.

10. The computational model of claim 7, wherein said pelvic environment comprises a vagina and said penetrating device is absorbent, and said model models the interaction of said human vagina when said penetrating device is inserted into said vagina, expands, and applies pressure to said vagina.

11. The computational model of claim 10, wherein said penetrating device is a tampon.

12. The computational model of claim 7, wherein said pelvic environment comprises a vagina and a cervix.

13. The computational model of claim 12, wherein said vagina is modeled as segmented tissue regions including recto-vaginal tissue and vesico-vaginal tissue.

14. The computational model of claim 7, wherein said material parameter and said boundary condition are defined by inverse finite element analysis.

* * * * *

UNITED STATES PATENT AND TRADEMARK OFFICE
CERTIFICATE OF CORRECTION

| | | |
|---|---|---|
| PATENT NO. | : 7,937,249 B2 | Page 1 of 1 |
| APPLICATION NO. | : 11/181280 | |
| DATED | : May 3, 2011 | |
| INVENTOR(S) | : Thomas Ward Osborn, III et al. | |

It is certified that error appears in the above-identified patent and that said Letters Patent is hereby corrected as shown below:

Column 4

Lines 42-43, delete "Tagadermg" and insert --Tagaderm®--.

Column 7

Line 24, delete "in-vitrQ" and insert --in-vitro--.

Column 10

Line 30, delete "$\mathcal{E}_z$" and insert --$\varepsilon_z$--.

Column 13

Line 12, delete "p g h" and insert --*p g h*--.

Line 12, delete "p" and insert --*p*--.

Line 13, delete "g" and insert --*g*--.

Line 13, delete "h" and insert --*h*--.

Column 15

Line 17, delete "$\mathcal{E}$" and insert --$\varepsilon$--.

Column 18

Line 8, delete "1.5 Echo" and insert --1.5 T Echo--.

Signed and Sealed this
Sixth Day of March, 2012

David J. Kappos
*Director of the United States Patent and Trademark Office*